(12) United States Patent
Sakanoue et al.

(10) Patent No.: US 8,012,488 B2
(45) Date of Patent: Sep. 6, 2011

(54) POLYOXYALKYLENE DERIVATIVE

(75) Inventors: Kenji Sakanoue, Kawasaki (JP);
Kenichiro Nakamoto, Kawasaki (JP);
Yuji Yamamoto, Kawasaki (JP); Hiroki Yoshioka, Kawasaki (JP)

(73) Assignee: NOF Corporation, Tokyo (JP)

( * ) Notice: Subject to any disclaimer, the term of this patent is extended or adjusted under 35 U.S.C. 154(b) by 328 days.

(21) Appl. No.: 11/816,611

(22) PCT Filed: Feb. 17, 2006

(86) PCT No.: PCT/JP2006/303359
§ 371 (c)(1),
(2), (4) Date: Sep. 13, 2007

(87) PCT Pub. No.: WO2006/088248
PCT Pub. Date: Aug. 24, 2006

(65) Prior Publication Data
US 2009/0023859 A1 Jan. 22, 2009

(30) Foreign Application Priority Data
Feb. 18, 2005 (JP) ................................. 2005-041523

(51) Int. Cl.
*A61K 39/385* (2006.01)
(52) U.S. Cl. ................... 424/194.1; 514/21.5; 514/21.6; 514/21.7; 514/21.8; 514/21.9; 514/716; 514/773; 525/430; 530/345
(58) Field of Classification Search ............. 514/15, 514/16, 17, 18, 19, 716, 773, 21.5, 21.6, 514/21.7, 21.8, 21.9; 525/54.1, 430; 530/345; 424/194.1
See application file for complete search history.

(56) References Cited

U.S. PATENT DOCUMENTS

| 5,643,575 | A |   | 7/1997 | Martinez et al. |
| 5,932,462 | A |   | 8/1999 | Harris et al. |
| 6,433,135 | B1 | * | 8/2002 | El-Tayar et al. ............. 530/313 |
| 2004/0072341 | A1 | * | 4/2004 | Katinger et al. ............. 435/325 |
| 2004/0204548 | A1 |   | 10/2004 | Kozlowski et al. |
| 2005/0058620 | A1 | * | 3/2005 | Nakamoto et al. ......... 424/78.38 |
| 2005/0063936 | A1 | * | 3/2005 | Yamasaki et al. .......... 424/78.27 |

FOREIGN PATENT DOCUMENTS

| CA | 2 502 948 A1 | 6/2004 |
| EP | 1 400 550 A1 | 3/2004 |
| JP | 04-021636 A | 1/1992 |
| JP | 2001-515522 A | 9/2001 |
| JP | 2004-197077 A | 7/2004 |
| JP | 2006-025766 A | 2/2006 |
| WO | WO 91/01758 A1 | 2/1991 |
| WO | WO 98/31383 A1 | 7/1998 |
| WO | WO 99/36100 A2 | 7/1999 |
| WO | WO 02/060978 * | 8/2002 |
| WO | WO 02/060978 A1 | 8/2002 |
| WO | WO 2004/046222 * | 6/2004 |

OTHER PUBLICATIONS

Zalipsky, S.; Advanced Drug Delivery Reviews, 16, 1995, p. 157-182.*
Roberts, M.J.; Bentley, M.D.; Harris, J.M.; Advanced Drug Delivery Reviews, 54, 2002, p. 459-476.*
Greene, T.W.; Wuts, P.G.M.; Protective Groups in Organic Synthesis, 1999, p. 17, 18, 23-26, 67-72.*
Furin et al., *European Journal of Medical Chemistry*, 38: 739-749 (2003).

* cited by examiner

*Primary Examiner* — David Wu
*Assistant Examiner* — Robert Jones
(74) *Attorney, Agent, or Firm* — Leydig, Voit & Mayer, Ltd.

(57) ABSTRACT

A novel polyoxyalkylene derivative represented by the following formula (1), wherein each symbol is as defined in the specification, which has a functional group capable of reacting with various physiologically active substances according to the object is provided.

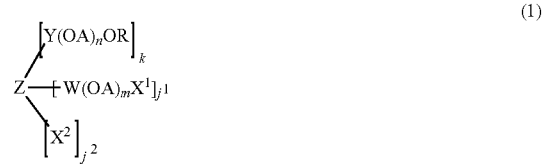

(1)

17 Claims, No Drawings

SEQUENCE LISTING

```
<160> NUMBER OF SEQ ID NOS: 4

<210> SEQ ID NO 1
<211> LENGTH: 5
<212> TYPE: PRT
<213> ORGANISM: Artificial
<220> FEATURE:
<223> OTHER INFORMATION: A part of polyoxyalkylene of the present
      invention

<400> SEQUENCE: 1

Gly Lys Gly Gly Gly
1               5

<210> SEQ ID NO 2
<211> LENGTH: 4
<212> TYPE: PRT
<213> ORGANISM: Artificial
<220> FEATURE:
<223> OTHER INFORMATION: A part of polyoxyalkylene of the present
      invention

<400> SEQUENCE: 2

Gly Lys Gly Gly
1

<210> SEQ ID NO 3
<211> LENGTH: 4
<212> TYPE: PRT
<213> ORGANISM: Artificial
<220> FEATURE:
<223> OTHER INFORMATION: A part of polyoxyalkylene of the present
      invention

<400> SEQUENCE: 3
```

```
Gly Gly Glu Gly
1

<210> SEQ ID NO 4
<211> LENGTH: 4
<212> TYPE: PRT
<213> ORGANISM: Artificial
<220> FEATURE:
<223> OTHER INFORMATION: Tetralysine

<400> SEQUENCE: 4

Lys Lys Lys Lys
1
```

POLYOXYALKYLENE DERIVATIVE

INCORPORATION-BY-REFERENCE OF MATERIAL ELECTRONICALLY SUBMITTED

Incorporated by reference in its entirety herein is the computer-readable nucleotide/amino acid sequence listing submitted on Aug. 17, 2007, and identified as follows: 928 bytes ASCII (Text) file named "701815SequenceListing.txt," created Aug. 17, 2007.

TECHNICAL FIELD

The present invention relates to a polyoxyalkylene derivative that modifies a biologically-relevant material.

BACKGROUND ART

In recent years, proteins, polypeptides, synthetic compounds, compounds extracted from natural resources and the like having a physiological activity have been found in a large number, and the application thereof to pharmaceutical products has been actively studied. However, such physiologically active substances show a short serum half-life when administered in vivo, and a sufficient pharmacological effect is often difficult to achieve. This is because, in general, a physiologically active substance administered in vivo mostly disappears from the body due to glomerular filtration in the kidney, macrophage uptake in the liver or spleen, and the like. Accordingly, attempts have been made to improve in vivo behavior by including such physiologically active substance in a liposome or polymer micelle, increasing the molecular weight by chemically modifying polyethylene glycol, which is an amphiphilic polymer, and the like. Polyethylene glycol shows low interaction with other biogenic substances due to its steric repulsion effect and the hydrated layer it has. As a result, a polypeptide (e.g., protein, enzyme etc.) modified with polyethylene glycol can avoid biological reactions such as glomerular filtration in the kidney, immunoreaction and the like when administered to the body, thus affording a longer serum half-life than non-modified ones. In addition, modification with polyethylene glycol affords the effect of lowering the toxicity and antigenicity of the modified substance, and further enhances the solubility of a highly hydrophobic, slightly water-soluble compound.

Conventionally, when a physiologically active substance is to be modified with polyethylene glycol, particularly when a low molecular weight pharmaceutical agent or peptide is to be modified, only a few kinds of reactive functional groups can be used for modification with polyethylene glycol. Moreover, when a number of polyethylene glycol molecules are used for the modification to ensure a sufficient effect of modification with polyethylene glycol, problem occurs in that the active sites of peptide or pharmaceutical agent, which is the substance to be modified, are blocked, thus preventing sufficient expression of the function and efficacy possessed by the substances themselves to be modified, or sufficient water solubility cannot be afforded.

To solve such problems, attempts have been made to use a branched polyethylene glycol derivative that reduces the sites modified by polyethylene glycol. JP-B-61-42558 proposes polyethylene glycol-modified L-asparaginase, and discloses a derivative wherein two polyethylene glycols as reactive polyethylene glycol are bonded to cyanuric chloride. However, cyanuric chloride, which is a starting material of the reactive polyethylene glycol derivative, has three reactive sites having equivalent reactivity. Thus, it is difficult to synthesize highly pure polyethylene glycol-modified L-asparaginase by selectively introducing thereinto two different polyethylene glycol chains.

Moreover, U.S. Pat. Nos. 5,643,575 and 5,932,462 propose branched polyalkylene glycol derivatives, suggesting a derivative having two or more polyalkylene glycol chains. Specifically, however, only a two-branch type having two polyalkylene glycol chains is disclosed. Furthermore, WO02/060978 proposes a branched derivative having three or more polyalkylene glycol chains. However, the polyalkylene glycol chain used does not have a terminal functional group. Specifically, only a compound having one kind of functional group, wherein the same polyalkylene glycol chains are bonded to equivalent groups, is disclosed. From the aspect of production process, it is difficult to introduce various polyalkylene glycol chains and many kinds of functional groups into the compound.

DISCLOSURE OF THE INVENTION

An object of the present invention is to provide a polyoxyalkylene derivative permitting optional adjustment of the kind and number, as well as a binding mode of the polyalkylene glycol chain, and further, the kind and number of the functional group.

More particularly, an object of the present invention is to provide a novel polyalkylene glycol derivative having plural polyalkylene glycol chains, which is afforded by binding a polyoxyalkylene compound with a functional group derived from a peptide in the structure and functional groups capable of reacting with various physiologically active substances depending on the object thereof. Since the functional group is bonded via a peptide chain or a polyoxyalkylene chain, it can react with various physiologically active substances.

Accordingly, the present invention is shown below.

[1] A polyoxyalkylene derivative represented by the following formula (1)

wherein

Z is a peptide residue consisting of 2 to 10 amino acid residues, wherein one or more amino acid residues have a side chain containing a functional group, OA is an oxyalkylene group having 2 to 4 carbon atoms, R is a hydrogen atom or a hydrocarbon group having 1 to 4 carbon atoms, $X^1$ and $X^2$ are groups containing a succinimide group, a maleimide group, an amino group, a carboxyl group, a carbonate group, an aldehyde group, a sulfonyl group, a thiol group, a vinyl group, an allyl group or a hydroxyl group, Y and W are each independently a divalent group containing a group selected from the group consisting of —CONH—, —NHCO—, —OCONH—, —NHOCO—, —COO—, —OOC—, —COS—, —SOC—, —CH$_2$NH—, —NHCH$_2$—, —S—CH<, >CH—S—, —CH$_2$—S—, —S—CH$_2$—, —S—S— and —O—, n is an integer of 5-1000, m is an integer of 5-800, $j^1$ is an integer of 0-12, $j^2$ is an integer of 0-8, k is an integer of 0-11, wherein $1 \leq j^1 + j^2 \leq 12$, $2 \leq k + j^1 \leq 12$, $3 \leq k + j^1 + j^2 \leq 12$, $30 \leq (n \times k) + (m \times j^1) \leq 2000$.

[2] The polyoxyalkylene derivative of the above-mentioned [1], wherein Z is a peptide residue consisting of 2 to 10 amino acid residues, wherein one or more amino acid residues have a side chain containing a functional group selected from the group consisting of an amino group, a carboxyl group, a thiol group and a hydroxyl group.

[3] The polyoxyalkylene derivative of the above-mentioned [2], wherein Z is a peptide residue consisting of 2 to 10 amino acid residues, wherein one or more amino acid residues are selected from the group consisting of lysin, aspartic acid, glutamic acid, cysteine and serine.

[4] The polyoxyalkylene derivative of the above-mentioned [3], wherein Z is a peptide residue consisting of 2 to 10 amino acid residues selected from the group consisting of lysin, aspartic acid and glutamic acid.

[5] The polyoxyalkylene derivative of any of the above-mentioned [1] to [4], wherein $j^1$ is 0, $j^2$ is 1-8 and k is 2-11.

[6] The polyoxyalkylene derivative of the above-mentioned [5], wherein $j^2$ is 1.

[7] The polyoxyalkylene derivative of any of the above-mentioned [1] to [4], wherein $j^1$ is 1-12.

[8] The polyoxyalkylene derivative of the above-mentioned [7], wherein $j^2$ is 0.

[9] The polyoxyalkylene derivative of the above-mentioned [7] or [8], wherein $j^1$ is 1.

[10] The polyoxyalkylene derivative of the above-mentioned [7], wherein $j^1$ is 2-12.

[11] The polyoxyalkylene derivative of the above-mentioned [7], wherein $j^2$ is 1-8.

[12] The polyoxyalkylene derivative of any of the above-mentioned [1] to [11], wherein Z is a peptide residue consisting of 3 to 8 amino acid residues, wherein one or more amino acid residues are selected from the group consisting of glycine, lysin, glutamic acid, cysteine and aspartic acid, k is 3-5.

[13] The polyoxyalkylene derivative of any of the above-mentioned [1] to [12], wherein R is a methyl group and OA is an oxyethylene group.

[14] The polyoxyalkylene derivative of any of the above-mentioned [1] to [13], wherein $X^1$ and $X^2$ are each independently a group selected from the group consisting of the following formulas (a)-(p):

(a)
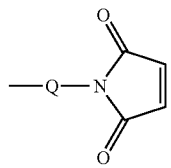

(b)
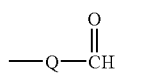

(c)
—Q—SH (d)
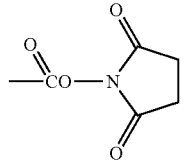

(e)
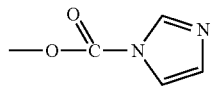

(f)
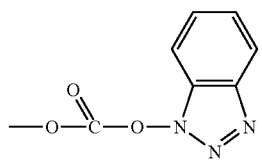

(g)
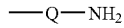

(h)

(i)
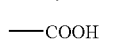

(j)
—Q—NH$_2$ (k)
—NH$_2$ (l)
—Q—COOH (m)
—COOH (n)
—SH (o)
—OH (p)
—Q—CH=CH$_2$ wherein Q is an alkylene group or an alkylene group having an ester bond, an amide bond, an ether bond, a urethane bond, a urea bond, a carbonate bond, a sulfide bond, an imine bond or a secondary amino group, and V is a hydrocarbon group having 1 to 10 carbon atoms optionally containing a fluorine atom.

DETAILED DESCRIPTION OF THE INVENTION

The polyoxyalkylene derivative of the present invention is represented by the formula (1):

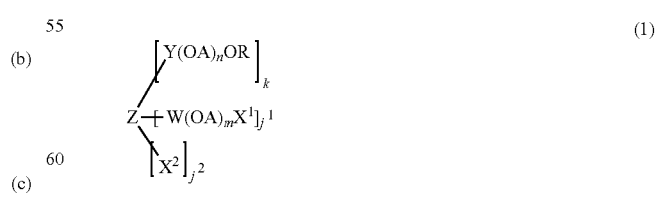

(1)

The definition of each symbol in the formula (1) is as follows.

Z is a peptide residue consisting of 2 to 10 amino acid residues, wherein one or more amino acid residues have a side chain containing a functional group. As used herein, the peptide residue refers to the part of a peptide chain except the terminal functional group and the functional group on the side chain. Examples of the terminal functional group include amino group and carboxyl group, examples of the functional group on the side chain include amino group, guanidino group, imidazolyl group, carboxyl group, carbamide group, hydroxyl group and thiol group. The functional group may be protected. Examples of the amino acid having a side chain containing a functional group include lysin, ornithine, arginine, histidine, aspartic acid, glutamic acid, γ-carboxyglutamic acid, serine, threonine, tyrosine, 4-hydroxyproline, cysteine and cystine. The peptide residue is not particularly limited as long as it contains at least one amino acid residue having a side chain containing a functional group and may be a synthetic substance or a naturally occurring substance. A peptide residue containing at least one residue selected from lysin and ornithine residues having an amino group on the side chain, aspartic acid, glutamic acid and γ-carboxyglutamic acid residues having a carboxyl group on the side chain, serine residue having a hydroxyl group on the side chain, and cysteine residue having a thiol group on the side chain is preferable, a peptide residue containing at least one residue selected from lysin, aspartic acid, glutamic acid, cysteine and serine is more preferable, and a peptide residue containing at least one residue selected from lysin, aspartic acid and glutamic acid is still more preferable.

Particularly preferable example of Z is a peptide residue consisting of 3 to 8 amino acid residues selected from the group consisting of glycine, lysin, glutamic acid, cysteine and aspartic acid.

OA is an oxyalkylene group having 2 to 4 carbon atoms, preferably an oxyethylene group.

$(OA)_n$ and $(OA)_m$ are each independently a polyoxyalkylene group having the above-mentioned oxyalkylene group having 2 to 4 carbon atoms as a constituent unit. The polyoxyalkylene group may be linear or branched. When the polyoxyalkylene group consists of two or more kinds of oxyalkylene groups, the mode of addition of alkylene oxide may be block or random.

Y is a group formed by the reaction of a polyoxyalkylene compound having a group selected from the following formulas (a)-(k) on the terminal of polyoxyalkylene chain represented by $(OA)_n$ with amino group, guanidino group, imidazolyl group, carboxyl group, carbamide group, hydroxyl group or thiol group in the peptide residue for Z, and is a Z-$(OA)_n$ binding group.

W is a binding group that binds a functional group represented by $X^1$ and Z via a polyoxyalkylene chain represented by $(OA)_m$.

Specifically, Y and W are each independently a divalent group containing a group selected from the group consisting of —CONH—, —NHCO—, —OCONH—, —NHOCO—, —COO—, —OOC—, —COS—, —SOC—, —CH₂NH—, —NHCH₂—, —NHCONH—, —S—CH<, >CH—S—, —CH₂—S—, —S—CH₂—, —S—S— and —O—.

Y and W are preferably divalent groups containing a group selected from the group consisting of —CONH—, —NHCO—, —OCONH—, —NHOCO—, —COO—, —OOC—, —CH₂NH—, —NHCH₂—, —S—CH< and >CH—S—.

Particularly preferable examples of Y and W include —NHCO—, —CONH(CH₂)₃O—, —NHCO(CH₂)₅—, —NH(CH₂)₃—, —CO(CH₂)₃CONH(CH₂)₃O— and

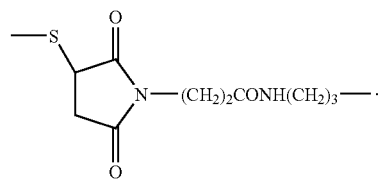

$X^1$ and $X^2$ are not particularly limited as long as they are functional groups capable of forming a chemical bond with a biologically-relevant material. Examples of $X^1$ and $X^2$ include groups containing succinimide group, maleimide group, amino group, carboxyl group, carbonate group, aldehyde group, sulfonyl group, thiol group, vinyl group, allyl group or hydroxyl group. In a preferably embodiment, $X^1$ and $X^2$ are each independently a group selected from the following formulas (a)-(p), which reacts with amino group, carboxyl group, aldehyde group, hydroxyl group, thiol group etc. contained in the biologically-relevant material. $X^1$ is a functional group on the terminal of polyoxyalkylene chain represented by $(OA)_m$, into which a protecting group may be introduced. $X^2$ is a group bonded to peptide without via polyoxyalkylene group or polyoxyalkylene chain. When a plurality of $X^1$ and $X^2$ exist, each may be independently the same or different.

(a)

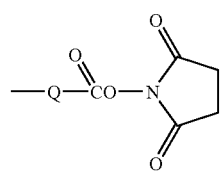

(b)

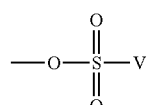

(c)

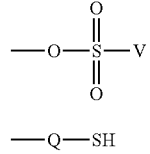

(d)

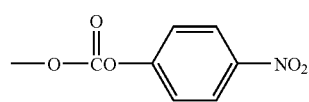

(e)

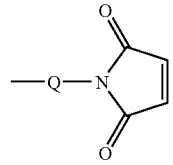

(f)

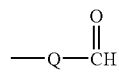

(g)

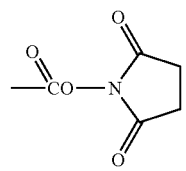

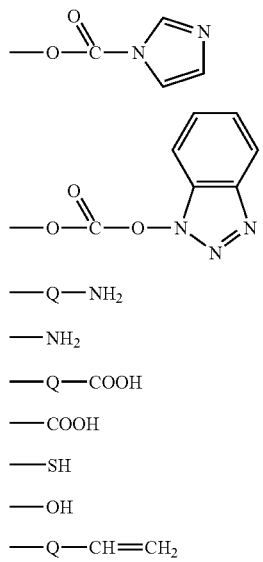

(h)

(i)

—Q—NH$_2$ (j)

—NH$_2$ (k)

—Q—COOH (l)

—COOH (m)

—SH (n)

—OH (o)

—Q—CH=CH$_2$ (p)

For reaction with an amino group in the biologically-relevant material, a group represented by (a), (b), (d), (f), (g), (h), (i), (l) or (m) is preferable; for reaction with a thiol group in the biologically-relevant material, a group represented by (a), (c), (e), (g), (l), (m), (n) or (p) is preferable; for reaction with an unsaturated bond in the biologically-relevant material, a group represented by (c) or (n) is preferable; and for reaction with a carboxyl group in the biologically-relevant material, a group represented by (c), (j), (k) or (n) is preferable.

Q in (a), (c), (e), (f), (j), (l) and (p) for $X^1$ or $X^2$ is a linker between polyoxyalkylene chain represented by (OA), or peptide residue for Z, and a functional group and, which is not particularly limited as long as it forms a covalent bond. Preferable examples include alkylene group and alkylene group containing ester bond, amide bond, ether bond, urethane bond, urea bond, carbonate bond, sulfide bond, imine bond or secondary amino group, and the like. Preferable examples of the alkylene group include methylene group, ethylene group, propylene group, butylene group, isopropylene group, isobutylene group and the like, and more preferable examples include ethylene group and propylene group. Preferable example of the alkylene group containing an ester bond is a structure as shown in the following (t1). Preferable example of the alkylene group containing an amide bond is a structure as shown in the following (t2). Preferable examples of the alkylene group containing an ether bond include structures as shown in the following (t3) and (t4). Preferable example of the alkylene group containing a urethane bond is a structure as shown in the following (t5). Preferable example of the alkylene group containing a urea bond is a structure as shown in the following (t6). Preferable example of the alkylene group containing a carbonate bond is a structure as shown in the following (t7). Preferable example of the alkylene group containing a sulfide bond is a structure as shown in the following (t8). Preferable example of the alkylene group containing an imine bond or secondary amino group is a structure as shown in the following (t9). In each formula, q is an integer of 1-6, preferably an integer of 1-3, more preferably 2 or 3. In (t2), (t6) and (t9), a plurality of q are contained in the formulas. They may be the same or different. In (t4), r is an integer of 1-5, preferably 1 or 2.

 (t1)

 (t2)

 (t3)

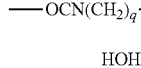 (t4)

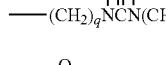 (t5)

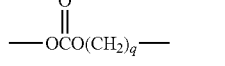 (t6)

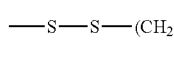 (t7)

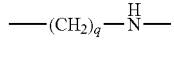 (t8)

 (t9)

V is a hydrocarbon group having 1 to 10 carbon atoms and optionally containing a fluorine atom. Specific examples include methyl group, ethyl group, propyl group, isopropyl group, butyl group, t-butyl group, hexyl group, nonyl group, vinyl group, phenyl group, benzyl group, 4-methylphenyl group, trifluoromethyl group, 2,2,2-trifluoroethyl group, 4-(trifluoromethoxy)phenyl group and the like, with preference given to methyl group, vinyl group, 4-methylphenyl group and 2,2,2-trifluoroethyl group.

When $X^2$ is a functional group represented by (k), (m), (n) or (o), $X^2$ is a functional group derived from a peptide residue for Z, for example, amino group derived from amino terminus or side chain of basic amino acid, carboxyl group derived from carboxyl terminus or side chain of acidic amino acid, hydroxyl group of serine residue and the like and thiol group of cysteine residue and the like.

R is a hydrogen atom or a hydrocarbon group having 1 to 4 carbon atoms, with preference given to alkyl group. Examples of the alkyl group include methyl group, ethyl group, propyl group, butyl group and the like. Of these, methyl group is preferable.

k is the number of polyoxyalkylene chains free of a functional group, and is an integer of 0-11. When $j^1$ is 0, it is an integer of 2-11. When k is not less than 2, respective polyoxyalkylene chains represented by $(OA)_n$ may be the same kind of polyoxyalkylene chains, or different kinds of polyoxyalkylene chains.

$j^1$ is the number of polyoxyalkylene chain having a functional group $X^1$, and is an integer of 0-12, preferably an integer of 1-12. When $j^1$ is not less than 2, respective polyoxyalkylene chains represented by $(OA)_m$ may be the same kind of polyoxyalkylene chains, or different kinds of polyoxyalkylene chains, as long as a functional group represented by $X^1$ is bonded to the terminal of each polyoxyalkylene chain.

$j^2$ is the number of functional groups $X^2$ bonded to Z without via a polyoxyalkylene chain, and is an integer of 0-8.

When $j^1$ or $j^2$ is not less than 2, functional groups for $X^1$ and $X^2$ may be each independently the same or different.

$k+j^1$ is the number of the polyoxyalkylene chains in the present compound and is an integer of 2-12, preferably an integer of 3-8.

When $j^1$ is 0, k is an integer of 2-11, preferably 2-8, more preferably 2-6, $j^2$ is an integer of 1-8, preferably 1-6, more preferably 1 or 2.

When $j^2$ is 0, k is an integer of 0-11, preferably 0-7, $j^1$ is an integer of 1-12, preferably 1-8, and $k+j^1$ is an integer of 2-12, preferably 2-8.

When $j^1$ is 1, k is preferably an integer of 2-8, more preferably 3-6, and $j^2$ is preferably 0.

When $j^1$ is 2, k is preferably an integer of 1-8, more preferably 1-4, and $j^2$ is preferably 0.

When $j^2$ is 1, k is preferably an integer of 0-4, $j^1$ is preferably an integer of 0-5.

When $j^1$ and $j^2$ are each not less than 1, k is an integer of 1-10, preferably 1-5.

$j^1+j^2$ is the number of the functional groups in the polyoxyalkylene derivative of the present invention, and is an integer of 1-12, preferably 1-8.

n and m each show an average addition mole number of an oxyalkylene group having 2 to 4 carbon atoms, n is an integer of 5-1000, preferably 20-800, and m is an integer of 5-800, preferably 10-700. They are such integers with which $(n \times k)+(m \times j^1)$ satisfies 30-2000, preferably 40-1200.

When the average addition mole number of the oxyalkylene group per one polyoxyalkylene chain for $(OA)_n$ or $(OA)_m$ is less than 5, or the average addition mole number of the whole oxyalkylene group $(n \times k)+(m \times j^1)$ is less than 30, the hydrated layer stabilizing the biologically-relevant material to be modified cannot be maintained sufficiently, and the stability becomes insufficient. When the average addition mole number of the oxyalkylene group per one polyoxyalkylene chain for $(OA)_n$ is greater than 1000, or the average addition mole number of the whole oxyalkylene group $(n \times k)+(m \times j^1)$ is greater than 2000 and a solution is prepared, the solution shows high viscosity, poor workability, and difficult handling. When a pharmaceutical product is prepared, excretion of the product from the body tends to be difficult. When the average addition mole number of the oxyalkylene group per one polyoxyalkylene chain for $(OA)_m$ is greater than 800 and a solution is prepared, the solution shows high viscosity, poor reactivity when a functional group for $X^1$ is introduced into the terminal, and difficult handling.

The average molecular weight of the polyoxyalkylene derivative of the present invention is preferably 1300-88000, more preferably 2000-55000, and still more preferably 5000-50000. When the molecular weight is less than 1300, the hydrated layer stabilizing the biologically-relevant material to be modified cannot be maintained sufficiently, and the stability becomes insufficient. When it is greater than 88000 and a solution is prepared, the solution shows high viscosity, poor workability, and difficult handling. When a pharmaceutical product is prepared, excretion of the product from the body tends to be difficult.

When $j^1$ is 0 and $j^2$ is not less than 1, the obtained compound has one or more functional groups that directly bind to the peptide residue and has no functional group at the polyoxyalkylene chain terminal. In this case, by binding the functional group directly bonded to the peptide residue with a biologically-relevant material during modification of the biologically-relevant material, plural polyoxyalkylene chains can be attached at a small number of binding sites when $j^2$ is 1, and further, the molecular weight of each polyoxyalkylene chain and the binding mode with the peptide chain can be appropriately changed. For stabilization of a biologically-relevant material, k is an integer of 2-11, preferably 2-6.

When $j^2$ is not less than 2, a plurality of the same or different biologically-relevant materials (for example, plural proteins or protein and pharmaceutical agent etc.) can be bound to the polyoxyalkylene derivative of the present invention, and respective binding modes can be changed appropriately. Therefore, the stability of a biologically-relevant material, and further, the in vivo stability of a preparation can be appropriately controlled.

When $j^2$ is 0 and $j^1$ is not less than 1, the obtained compound has a functional group at the polyoxyalkylene chain terminal, and no functional group directly binding with the peptide. In this case, the stability of a biologically-relevant material and in vivo stability of a preparation can be controlled by modification of a biologically-relevant material. In addition, the following can also be possible. When $j^1$ is 1, k is an integer of 2-11, preferably 2-6, for stabilization of a biologically-relevant material. When $j^1$ is 1, even if a binding site is absent on the surface of a biologically-relevant material and a reaction is difficult for the functional group for $X^2$, a reaction with the biologically-relevant material is advantageously facilitated since a functional group is present at the polyoxyalkylene chain terminal. When $j^1$ is not less than 2 and plural biologically-relevant materials are to be bound with one molecule of polyoxyalkylene derivative, binding of plural proteins and the like having large molecular weights thereto is sometimes difficult due to steric hindrance since functional groups $X^2$ derived from the peptide are adjacent to each other. In such case, when functional groups are present via a polyoxyalkylene chain, the steric hindrance can be reduced and binding of plural proteins and the like having large molecular weights can be facilitated. Similarly, when plural functional groups are present on a polyoxyalkylene chain terminal, the steric hindrance does not pose a problem and proteins can be crosslinked for polymerization.

When both $j^1$ and $j^2$ are not less than 1, the obtained compound has a functional group directly binding to peptide, and a polyoxyalkylene chain having a functional group at the terminal. In this case, the functional group binding to the peptide and the functional group binding to the polyoxyalkylene chain terminal may be different from each other. When $k+j^1$ is not less than 2, the stability of the biologically-relevant material to be modified, the in vivo stability of a preparation can be controlled, and plural biologically-relevant materials can be bound. $j^1$ is preferably 1-4 since $X^1$ may be bound with a protein and the like having high molecular weights, and $j^2$ is preferably 2-6 since a target product unaffected by steric hindrance or a low molecular weight substance may be fixed on $X^2$. For example, when $j^1$ is 2 and $j^2$ is 1, an antibody for which a binding site is absent on the surface and having low reactivity is bound via one $X^1$, a marker such as a fluorescent substance and the like is bound via the other $X^1$, and the derivative is bound on the base via $X^2$, whereby a microplate and the like having high function can be obtained. Similarly, for example, when $j^1$ is 1 and $j^2$ is not less than 2, a derivative wherein an antibody and the like are bound via $X^1$ in an attempt to reach the target site, and plural pharmaceutical agents are bound via $X^2$, can be obtained.

The production methods of the polyoxyalkylene derivative of the present invention are explained in the following. The polyoxyalkylene derivative of the present invention can be produced by a known method. For example, the derivative can be produced by the following methods.

(i) A method comprising reacting a peptide with a polyoxyalkylene compound, and a method comprising denaturing $X^2$ or $X^1$ thereafter and introducing a different functional group.

(ii) A method comprising binding a polyoxyalkylene compound having, on one terminal, a functional group that can be $X^1$ in the formula (1) and a functional group involved in the reaction with a peptide at the other terminal with the peptide. In this method, a protecting group may be introduced into the functional group that can be $X^1$ in the formula (1), which is on one terminal of the polyoxyalkylene compound, to avoid its involvement in the binding with the peptide, after which the compound may be reacted with the peptide. The protecting group can be eliminated according to the object to afford functional group $X^1$.

(iii) A method of synthesizing a polyoxyalkylene derivative by reacting amino acid with a polyoxyalkylene compound, and condensing the compound with other amino acid. In this method, the obtained compound may be further reacted with a polyoxyalkylene compound, or $X^2$ or $X^1$ may be denatured and other functional group may be introduced.

Any one of the above-mentioned methods (i)-(iii) may be used, or they may be appropriately combined. The reaction between a peptide and a polyoxyalkylene compound can be performed according to a known method. Specifically, for example, the methods described in the following production methods 1-18 can be employed. In the synthesis steps, the amino group, carboxyl group and other functional groups of peptide can be protected by the protecting groups described in Nobuo Izumiya, et al.: Peptide Gosei-no-Kiso to Jikken (Basics and experiments of peptide synthesis), published by Maruzen Co. (1975).

Production examples using the method of (i) is shown below.

<Binding Method of Peptide and Polyoxyalkylene Chain>
(Production Method 1: W and Y are Divalent Groups Containing —NHCO—)

As the polyoxyalkylene compound, for example, a polyoxyalkylene carboxylic acid compound wherein the terminal of polyoxyalkylene chain represented by $(OA)_n$, $(OA)_m$ is carboxylic acid represented by the above-mentioned formula (1) can be used.

The terminal carboxyl group may be converted to an acid anhydride using a dehydrocondensation agent, or an activated ester. The dehydrocondensation agent is not particularly limited as long as it can condense, with dehydration, the carboxyl groups of a polyoxyalkylene carboxylic acid compound. Examples of such dehydrocondensation agent include carbodiimide derivatives such as dicyclohexylcarbodiimide and the like, and dicyclohexylcarbodiimide (DCC) is particularly preferable. The amount of the dehydrocondensation agent to be used is 1.05- to 5-fold by mole, preferably 1.5- to 2.5-fold by mole, of the polyoxyalkylene carboxylic acid compound.

Activated ester can be obtained, for example, by reacting a polyoxyalkylene carboxylic acid compound with an activator in the presence of a dehydrocondensation agent. While the kind of the activator is not particularly limited, it is, for example, N-hydroxysuccinimide, N,N'-disuccinimide carbonate, 1-hydroxybenzotriazole, N-hydroxy-5-norbornene-2,3-dicarboxylmide, N-hydroxyphthalimide, 4-hydroxyphenyldimethylsulfonium-methylsulfate, isobutylchloroformate and the like. Of these, N-hydroxysuccinimide is preferable. The amount of N-hydroxysuccinimide to be used is 0.1- to 2-fold by mole relative to the polyoxyalkylene carboxylic acid compound. With this amount, the yield may be enhanced in some cases.

When a polyoxyalkylene chain terminal is used as an activated ester compound, the method is not limited to those mentioned above, and the structure shown by the above-mentioned formula (a) can be used similarly. In this case, Q is as mentioned above.

Examples of the peptide include a peptide having an α-amino group at the N-terminus, and a peptide having an ε-amino group, i.e., a lysin residue. By reacting the above-mentioned polyoxyalkylene carboxylic acid compound with a peptide in the presence of a basic catalyst in an organic solvent, a polyoxyalkylene-peptide compound containing the above-mentioned divalent group can be produced at a high purity. While the amount of the polyoxyalkylene carboxylic acid compound to be used is not particularly limited, the equivalent ratio of polyoxyalkylene carboxylic acid compound and peptide is preferably 5:1-1:5.

As the organic solvent to be used for the reaction, any can be used without particular limitation as long as it does not have a reactive functional group such as hydroxyl group and the like. Examples of such organic solvent include acetonitrile, dimethylformamide, dimethylsulfoxide, dioxane, and mixed solvents of ethyl acetate, dichloromethane, chloroform, benzene, toluene and the like containing them. Of these, acetonitrile, dimethylformamide and dioxane are preferable because peptide is easily dissolved therein. When the peptide is hardly soluble in an organic solvent, a mixture of water or buffer and an organic solvent can also be used.

While the kind of the basic catalyst to be used for the reaction is not particularly limited, for example, nitrogen-containing substances such as triethylamine, pyridine, morpholine, ammonium acetate and the like, organic salts such as sodium phosphate, sodium carbonate, sodium hydrogencarbonate, sodium borate, sodium acetate and the like can be mentioned. The amount of the basic catalyst to be used is, for example, 1- to 10-fold by mole, preferably 1.2- to 5-fold by mole, relative to the polyoxyalkylene carboxylic acid compound. The reaction temperature is generally 0-90° C., preferably 15-50° C., more preferably 20-45° C. When it is lower than 0° C., the reaction rate may be low, and when it is higher than 90° C., a side reaction product may be produced. The reaction time is not less than 1 hr, preferably 2-24 hr.

After completion of the reaction, the compound can be purified by the following step. Crystals of the polyoxyalkylene-peptide compound can be obtained at a high purity by a method comprising, after filtration of insoluble materials from the reaction solution, concentrating the filtrate or feeding the filtrate into a poor solvent to allow crystallization and the like. By dissolving the obtained crystals and cooling or adding a poor solvent to allow crystal precipitation of the polyoxyalkylene-peptide compound, free peptide, dehydrocondensation agent, N-hydroxysuccinimide, dicyclohexylcarbodiimide and the like can be removed and the compound can be purified. As the solvent to be used for this step, a solvent capable of dissolving the obtained crystals, and crystal precipitation of the polyoxyalkylene-peptide compound by cooling, for example, ethyl acetate, alcohols such as isopropyl alcohol and the like, or a solvent capable of crystallizing the polyoxyalkylene-peptide compound by adding a poor solvent such as hexane, ether and the like is preferable.

After dissolving the obtained crystals in a solvent such as ethyl acetate and the like, impurities such as salt and the like are desirably removed by a method comprising adding an adsorbent and stirring and the like. Examples of the adsorbent include an adsorbent containing alkaline earth metal oxide (e.g., aluminum oxide, magnesium oxide), alkaline earth metal hydroxide (e.g., aluminum hydroxide, magnesium hydroxide), aluminum or silicon (e.g., silicon oxide), active carbon and the like. These adsorbents are commercially available. Examples thereof include Kyoward 200, Kyoward 300, Kyoward 500, Kyoward 600, Kyoward 700, Kyoward 1000, Kyoward 2000 (all of which are manufactured by Kyowa chemical Industry Co., Ltd., trademark), Tomix-AD300, Tomix-AD500, Tomix-AD700 (all of which are manufactured by Tomita Pharmaceutical Co., Ltd., trademark) and the like. The adsorbent may be used alone or in a combination of two kinds or more.

The temperature of the treatment using an adsorbent is 10° C. to 85° C., preferably 40° C. to 70° C., and the treatment time is 10 min-5 hr, preferably 30 min-3 hr. When the treatment temperature is lower than 10° C., crystals of polyoxyalkylene-peptide compound are precipitated and removed alongside when the adsorbent is removed, whereby the yield tends to decrease. When it exceeds 85° C., hydrolysis and the like of the polyoxyalkylene-peptide compound may occur due to the presence of a trace amount of water during the treatment with an adsorbent. The amount of the adsorbent to be used is 0.1-200 parts by weight, preferably 1-50 parts by weight, per 100 parts by weight of the crystals to be treated. After the treatment with an adsorbent, the adsorbent may be removed by a method such as filtration and the like, followed by crystallization by cooling or using a poor solvent. Cooling to 10° C. or below to allow crystallization preferably affords crystals in a good yield.

The amount of the solvent to be used in the above-mentioned step is 1- to 100-fold (volume), preferably 2- to 50-fold (volume), relative to the crystals. After recrystallization, crystallization is performed by cooling or using a poor solvent. Specific crystallization method includes the following method. That is, crystals of the polyoxyalkylene-peptide compound are precipitated by dissolving the compound in a solvent such as ethyl acetate, toluene, chloroform and the like, and adding a solvent such as ether or aliphatic hydrocarbon having 5 to 8 carbon atoms. Specifically, a method comprising dissolving the compound in ethyl acetate, and adding hexane to allow crystallization is preferable. While aliphatic hydrocarbon having 5 to 8 carbon atoms is not particularly limited, for example, pentane, isopentane, neopentane, hexane, isohexane, 3-methylpentane, neohexane, 2,3-dimethylbutane, heptane, 2-methylhexane, 3-methylhexane, 3-ethylpentane, 2,2-dimethylpentane, 2,3-dimethylpentane, 3,3-dimethylpentane, 2,3,3-trimethylbutane, octane, 2-methylheptane, 3-methylheptane, 4-methylheptane, 3-ethylhexane, 2,2-dimethylhexane, 2,3-dimethylhexane, 2,4-dimethylhexane, 2,5-dimethylhexane, 3,3-dimethylhexane, 3,4-dimethylhexane, 2-methyl-3-ethylpentane, 3-methyl-3-ethylpentane, 2,2,3-trimethylpentane, 2,2,4-trimethylpentane, 2,2,3,3-tetramethylbutane and the like can be used. Of these, hexane and heptane are preferable. When the purity of the crystal is to be further increased, a similar crystallization step is repeated several times, whereby a polyoxyalkylene-peptide compound having a more superior purity can be obtained.

(Production Method 2: when W and Y are Divalent Groups Containing —CONH—)

As the polyoxyalkylene compound, for example, a polyoxyalkylene amine compound wherein the aforementioned polyoxyalkylene chain terminal is an amino group represented by the above-mentioned formula (j) can be used.

As the peptide, for example, a peptide having a carboxyl group at the C-terminus, or a peptide having a glutamic acid residue or aspartic acid residue having a carboxyl group on the side chain can be used. The carboxyl group of a peptide may be converted to an activated ester using a dehydrocondensation agent and an activator. As the dehydrocondensation agent and activator in this case, a compound similar to those in the aforementioned production method 1 can be used. As the racemization preventing agent or active esterification agent for the peptide, 1-hydroxybenzotriazole is preferable. Alternatively, a polyoxyalkylene compound and a peptide may be dissolved in a solvent or buffer or water, and a dehydrocondensation agent is added to perform the reaction. As the dehydrocondensation agent, aqueous carbodiimide such as 1-ethyl-3-(3-dimethylaminopropyl)carbodiimide (EDC) and the like can also be used. Other activation conditions, solvent and the like are as those in the aforementioned production method 1.

By reacting a polyoxyalkylene amine compound with a peptide in the presence of a basic catalyst in a solvent similar to those in the above-mentioned production method 1, a polyoxyalkylene-peptide compound containing the above-mentioned divalent group can be produced at a high purity. While the amount of the polyoxyalkylene amine compound to be used is not particularly limited, the equivalent ratio of polyoxyalkylene amine compound and peptide is preferably 0.2:1-1:5. The purification step after the reaction can be performed in the same manner as in the aforementioned production method 1.

(Production Method 3: when W and Y are Divalent Groups Containing —NHCOO—)

As the polyoxyalkylene compound, for example, a polyoxyalkylene carbonate compound wherein the aforementioned polyoxyalkylene chain terminal is carbonated can be used. As the polyoxyalkylene carbonate compound, for example, polyoxyalkylene-(p-nitrophenylcarbonate) can be mentioned. As the peptide, for example, a peptide having an α-amino group at the N-terminus, or a peptide having a lysin residue having an ε-amino group can be used. By reacting a polyoxyalkylene carbonate compound with a peptide in the presence of a basic catalyst in an organic solvent, a polyoxyalkylene-peptide compound containing the above-mentioned divalent group can be produced at a high purity. While the amount of the polyoxyalkylene carbonate compound to be used is not particularly limited, the equivalent ratio of polyoxyalkylene carbonate compound and peptide is preferably 5:1-1:5. The reaction conditions and purification step are similar to those in the aforementioned production method 1.

(Production Method 4: when W and Y are Divalent Groups Containing —NHCH$_2$—)

As the polyoxyalkylene compound, for example, a polyoxyalkylene aldehyde compound wherein the aforementioned polyoxyalkylene chain terminal is an aldehyde group represented by the above-mentioned formula (f), or a polyoxyalkylene sulfonate compound wherein the terminal is a sulfonate group represented by the above-mentioned formula (b) can be used.

As the peptide, for example, a peptide having an α-amino group at the N-terminus of the aforementioned polyoxyalkylene group, or a peptide having a lysin residue having an ε-amino group can be used. By reacting a polyoxyalkylene aldehyde compound with a peptide in the presence of a reducing agent in a buffer, a polyoxyalkylene-peptide compound containing the above-mentioned divalent group can be produced at a high purity. While the amount of the polyoxyalkylene aldehyde compound to be used is not particularly limited, the molar ratio of polyoxyalkylene aldehyde compound and peptide is preferably 5:1-1:5.

As the above-mentioned buffer, acetate buffer, phosphate buffer, tris-acid buffer and the like are preferably used. Moreover, an organic solvent not involved in the reaction such as acetonitrile, dimethylsulfoxide, dimethylformamide, dimethylacetamide and the like may be further added. The pH during the reaction is pH2-8.5, preferably pH3-7. The reaction temperature is 0-90° C., and the reaction time is 0.5-20 hr, preferably 0.5-4 hr. When the above-mentioned reducing agent is not present, a Schiff base is formed. When a Schiff base is formed, it is reduced using a reducing agent such as sodium cyanoborohydride and the like to form a secondary amino group. After the reaction, the compound can be purified by a purification means such as dialysis, salting out, ultrafiltration, ion exchange chromatography, electrophoresis, extraction, recrystallization, adsorption treatment, reprecipitation, column chromatography and the like.

(Production Method 5: when W and Y are Divalent Groups Containing —COO—)

As the polyoxyalkylene compound, for example, a polyoxyalkylene compound wherein the terminal of the aforementioned polyoxyalkylene group is a hydroxyl group can be used. As the peptide, for example, a peptide having a carboxyl group at the C-terminus, or a peptide having a glutamic acid residue or aspartic acid residue having a carboxyl group on the side chain can be used. The reaction conditions and purification conditions are similar to those in the aforementioned production method 2.

(Production Method 6: when W and Y are Divalent Groups Containing —S—CH<)

As the polyoxyalkylene compound, for example, a polyoxyalkylene maleimide compound wherein the terminal of the aforementioned polyoxyalkylene group is a maleimide group represented by the above-mentioned formula (e) can be used. As a particularly preferable polyoxyalkylene maleimide compound, a polyoxyalkylene maleimide compound having a maleimide group represented by the following formula (y1)-(y3) can be mentioned. In the following formula, a is 2 or 3 and b is 2-5.

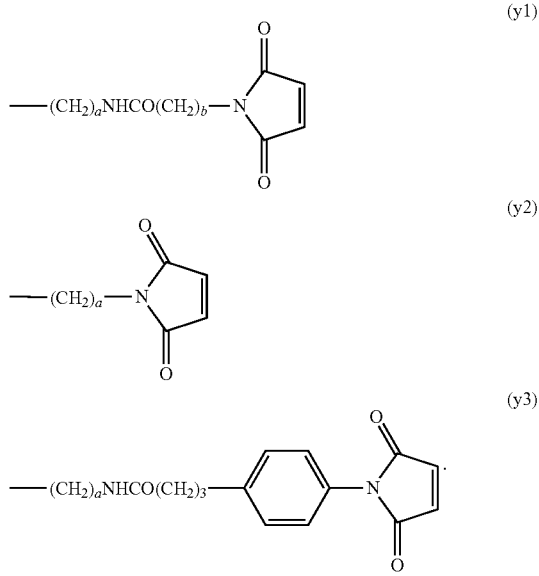

As the peptide, for example, a peptide having a thiol group derived from the cysteine residue, or a peptide having an amino acid residue into which a thiol group has been introduced using an iminothioran and the like can be used. By reacting the above-mentioned polyoxyalkylene maleimide compound with a peptide in water or buffer, a sulfide bond is formed. As the above-mentioned buffer for the reaction, buffers such as phosphate buffer, borate buffer, tris-acid buffer, acetate buffer and the like are preferable. In the same manner as in production method 4, an organic solvent may be added. While the reaction temperature is not particularly limited, it is preferably 0-80° C. The reaction time is preferably 0.5-72 hr, more preferably 1-24 hr.

The peptide-polyoxyalkylene bonded product obtained as mentioned above is converted to a compound of the following formula (2), and the terminal group thereof is converted to various reactive groups represented by the above-mentioned formulas (a)-(k) by the following production methods 7-12, whereby the compound of the present invention can be produced. In addition, a functional group derived from an amino acid residue of a peptide, for example, an amino group of an amino-terminus or side chain or a carboxyl group of a carboxy-terminus or side chain may be directly used as a reactive group. A group not involved in the reaction may remain in such a functional group.

wherein Z is a peptide residue consisting of 2-10 amino acid residues and having one or more amino acid residues having a functional group on the side chain, OA is an oxyalkylene group having 2 to 4 carbon atoms, R is a hydrogen atom or a hydrocarbon group having 1 to 4 carbon atoms, $Xp^1$ and $Xp^2$ are groups containing an amino group, a carboxyl group, a thiol group or a hydroxyl group, Y and W are each a divalent group containing a group selected from the group consisting of —CONH—, —NHCO—, —OCONH—, —NHOCO—, —COO—, —OOC—, —COS—, —SOC—, —CH$_2$NH—, —NHCH$_2$—, —S—CH<, >CH—S—, —CH$_2$—S—, —S—CH$_2$—, —S—S— and —O—, n and m are each an average addition mole number of oxyalkylene groups having 2 to 4 carbon atoms, n is an integer of 5-1000, m is an integer of 5-800, which satisfy (n×k)+(m×j$^1$)=30-2000, j$^1$ is an integer of 0-12, j$^2$ is an integer of 0-8, which satisfy $1 \leq j^1+j^2 \leq 12$, and k is an integer of 0-11, which satisfies $2<k+j^1 \leq 12$, $3 \leq k+j^1+j^2 \leq 12$.

<Binding Method of Terminal Functional Groups $X^1$ and $X^2$>

(Production Method 7: Production Method of (B), (D), (H) and (i))

By reacting a compound of the formula (2) with any of the compounds represented by the following formulas (b1), (d1), (h1), (h2) and (i1) in the presence of an organic base catalyst such as triethylamine, pyridine, 4-dimethylaminopyridine and the like or an inorganic base catalyst such as sodium carbonate, sodium hydroxide, sodium hydrogencarbonate, sodium acetate, potassium carbonate, potassium hydroxide and the like, without a solvent or in an aprotic solvent such as toluene, benzene, xylene, acetonitrile, ethyl acetate, diethyl ether, t-butyl-methyl ether, tetrahydrofuran, chloroform, methylene chloride, dimethylsulfoxide, dimethylformamide, dimethylacetamide and the like, (b), (d), (h) or (i) can be introduced. In addition, the above-mentioned organic base and inorganic base may not be used. While the proportion of the organic base and inorganic base to be used is not particularly limited, not less than equimole relative to the compound of the formula (2) is preferable. An organic base such as pyridine and the like may be used as a solvent. T in (b1), (d1) and (h2) is a halogen atom selected from Cl, Br and I, and is preferably Cl. While the proportion of the compound represented by the formula (b1), (d1), (h1), (h2) or (i1) to be used is not particularly limited, not less than equimole relative to the compound of the formula (2) is preferable and, more preferably, a reaction is preferably performed within the range of equimole to 50 mole. The reaction temperature is preferably 0° C. to 300° C., more preferably 20° C.-100° C. The reaction time is preferably 10 min-48 hr, more preferably 30 min-24 hr. The produced compound may be purified by a purification means such as extraction, recrystallization, adsorption treatment, reprecipitation, column chromatography, supercritical extraction and the like.

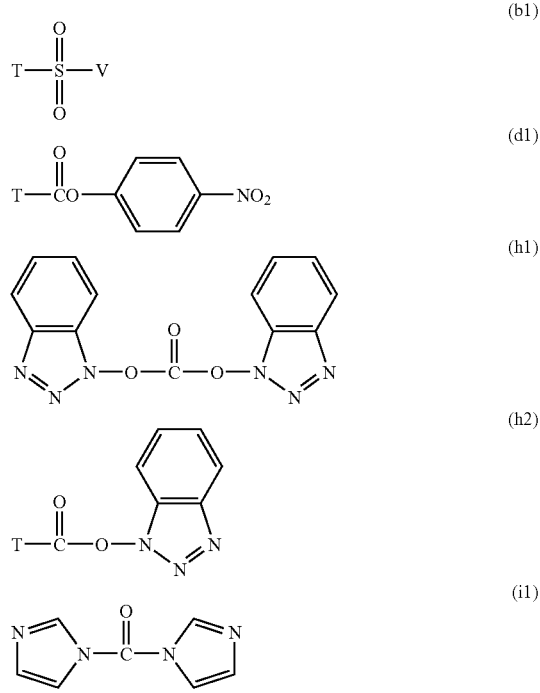

(Production Method 8: Production Method of (a) and (g))

After a compound of the formula (2) is reacted with a dicarbonic anhydride such as succinic anhydride, glutaric anhydride and the like to give carboxyl form (1), or when Xp$^1$ of the formula (2) is a carboxyl group (m) and Xp$^2$ of the formula (2) is a carboxyl group (m) or (l), the compound is subjected to a condensation reaction with N-hydroxysuccinimide in the presence of a condensation agent such as DCC, EDC and the like to give a succinimide form of (a) or (g). Besides N-hydroxysuccinimide, 1-hydroxybenzotriazole, N-hydroxy-5-norbornene-2,3-dicarboxylmide, N-hydroxyphthalimide, 4-hydroxyphenyldimethyl sulfonium-methyl sulfate and the like can be used. The reaction of the compound of the formula (2) with dicarbonic anhydride is performed in the aforementioned aprotic solvent or without solvent. While the proportion of the dicarbonic anhydride to be used is not particularly limited, not less than equimole relative to the compound of the formula (2) is preferable, and 1-5 equivalents is more preferable. The reaction temperature is preferably 0° C.-150° C., more preferably 20° C.-130° C. The reaction time is preferably 10 min-48 hr, more preferably 30 min-12 hr. An organic base such as triethylamine, pyridine, dimethylaminopyridine and the like, or an inorganic base such as sodium carbonate, sodium hydroxide, sodium hydrogencarbonate, sodium acetate, potassium carbonate, potassium hydroxide and the like may be used as a catalyst in the reaction. The proportion of the catalyst to be used is preferably 0.1-50 wt %, more preferably 0.5-20 wt %. The carboxyl form 1 produced in this way may be purified by the aforementioned purification means, or may be directly used for the next condensation reaction.

The subsequent condensation reaction is also performed in the above-mentioned aprotic solvent or without solvent. While the condensation agent is not particularly limited, it is preferably DCC. The proportion of the DCC to be used is preferably not less than one equivalent relative to the compound of the formula (2), more preferably 1-5 equivalents. The proportion of the N-hydroxysuccinimide to be used is preferably not less than one equivalent relative to the compound of the formula (2), more preferably 1-5 equivalents. The reaction temperature is preferably 0° C.-100° C., more preferably 20° C.-80° C. The reaction time is preferably 10 min-48 hr, more preferably 30 min-12 hr. The produced compound may be purified by the aforementioned purification means.

(Production Method 9: Production Method of (j))

Acrylonitrile and the like are added to a compound of the formula (2) in a solvent such as water, acetonitrile and the like, using an inorganic base such as sodium hydroxide, potassium hydroxide and the like as a catalyst to give a nitrile form, which is then subjected to a hydrogenation reaction of a nitrile group in an autoclave under a nickel or palladium catalyst to give an amine form (j). While the proportion of the inorganic base to be used to obtain the nitrile form is not particularly limited, it is preferably 0.01-50 wt % relative to the compound of the formula (2). While the proportion of the acrylonitrile and the like to be used is not particularly limited, it is preferably not less than equimolar relative to the compound of the formula (2), and a reaction within the range of equimole-100 mole is more preferable. In addition, acrylonitrile may be used as a solvent. The reaction temperature is preferably −50° C.-100° C., more preferably −20° C.-60° C. The reaction time is preferably 10 min-48 hr, more preferably 30 min-24 hr. While the reaction solvent for the subsequent hydrogenation reaction of nitrile form is not particularly limited as long as it is not involved in the reaction, it is preferably toluene. While the proportion of the nickel, or palladium catalyst to be used is not particularly limited, it is 0.05-30 wt %, preferably 0.5-5 wt %, relative to the nitrile form. The reaction temperature is preferably 20° C.-200° C., more preferably 50° C.-150° C. The reaction time is preferably 10 min-48 hr, more preferably 30 min-24 hr. The hydrogen pressure is preferably 2-10 MPa, more preferably 3-6 MPa. To prevent dimerization, ammonia may be added to the reaction system. When ammonia is added, the proportion thereof to be used is not particularly limited, but preferably 1-100 wt %, more preferably 5-50 wt %, relative to the nitrile form. The produced compound may be purified by the aforementioned purification means.

The above-mentioned amine form (j) can be obtained by reacting (b) with aqueous ammonia. The reaction is performed in aqueous ammonia, where the concentration of ammonia is not particularly limited, but preferably within the range of 10-40%. The proportion of the aqueous ammonia to be used is not particularly limited as long as the contained ammonia is not less than equimole of (b), and preferably equimole to 50000-fold mole. The reaction temperature is preferably 0° C.-100° C., more preferably 20° C.-80° C. The reaction time is preferably 10 min-48 hr, more preferably 30 min-12 hr. The produced compound may be purified by the aforementioned purification means.

(Production Method 10: Production Method of (e))

The maleimide form (e) can be obtained by reacting the following formula (e1) with amine of the aforementioned (j)

or the formula (2) wherein $Xp^1$ and $Xp^2$ are already (k). The reaction is performed in the aforementioned aprotic solvent or without solvent by adding an equivalent or more of compound (e1) to amine of (j) or (k). The proportion of the (e1) to be used is preferably one or more equivalents, more preferably equimole-5 moles, of (j) or (k). The reaction temperature is preferably 0° C.-200° C., more preferably 20° C.-80° C. The reaction time is preferably 10 min-48 hr, more preferably 30 min-12 hr. The produced compound may be purified by the aforementioned purification means.

As to the above-mentioned maleimide form, amine of (j) or (k) is reacted with maleic anhydride in the aforementioned aprotic solvent or without solvent to give a maleamide form, which is then subjected to ring closure reaction using acetic anhydride and sodium acetate as catalysts to give the maleimide form (e). While the proportion of the maleic anhydride to be used in the maleamidation reaction is not particularly limited, it is preferably not less than one equivalent, more preferably 1-5 equivalents, relative to the compound of the formula (2). The reaction temperature is preferably 0° C.-150° C., more preferably 20° C.-130° C. The reaction time is preferably 10 min-48 hr, more preferably 30 min-12 hr. The produced maleamide form may be purified by the aforementioned purification means, or used for the next ring closure reaction.

While the reaction solvent in the subsequent ring closure reaction is not particularly limited, an aprotic solvent or acetic anhydride is preferable. While the proportion of the acetic anhydride to be used is not particularly limited, it is preferably not less than equimole, more preferably equimole-50 moles, relative to the maleamide form. While the proportion of the sodium acetate to be used is not particularly limited, it is preferably 0.5-50 wt % relative to the maleamide form. The reaction temperature is preferably 0° C.-200° C., more preferably 20° C.-150° C. The reaction time is preferably 10 min-48 hr, more preferably 30 min-12 hr. The produced compound may be purified by the aforementioned purification means.

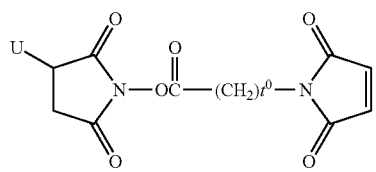

(e1)

wherein $t^0$ is 1-7 and U is a hydrogen atom or —$SO_3Na$.

(Production Method 11: Production Method of (f))

The aldehyde form (f) can be obtained by reacting compound (b) with acetal compound (f1) to give an acetal form, which is then subjected to hydrolysis under acidic conditions. The production of compound (b) is as mentioned above. Acetalization reaction can be performed by reacting (b) with equimole or above, preferably equimole-50 mole, of (f1) in the aforementioned aprotic solvent or without solvent. (f1) can be prepared from the corresponding alcohol using metal sodium, metal potassium, sodium hydride, potassium hydride, sodium methoxide, potassium t-butoxide and the like. The reaction temperature is preferably 0° C.-300° C., more preferably 20° C.-150° C. The reaction time is preferably 10 min-48 hr, more preferably 30 min-24 hr.

When (f2) is used, the hydroxyl group of $Xp^1$ and $Xp^2$ of compound (o) is converted to an alcoholate by the aforementioned method, and an acetal form can be obtained by reacting one or more equivalents, preferably 1-100 equivalents, of (f2) in the aforementioned aprotic solvent or without solvent. The reaction temperature is preferably 0-200° C., more preferably 20-130° C. The reaction time is preferably 10 min-48 hr, more preferably 30 min-24 hr.

When (f3) is used, an acetal form can be obtained by reacting (a), (b), (d), (g), (h), (i), (l) or (m) with (f3).

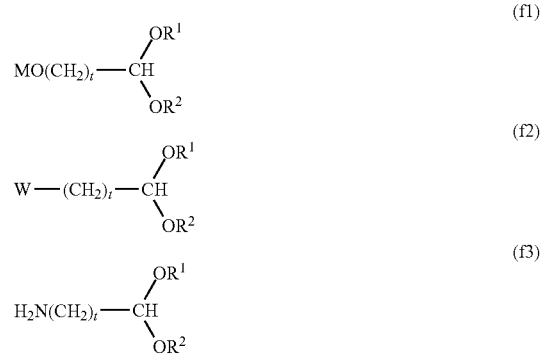

wherein $R^1$ and $R^2$ are hydrocarbon groups having 1 to 3 carbon atoms, which may be the same or different and may form ring with each other, M is sodium or potassium, W is a halogen atom selected from Cl, Br and I, and t is an integer of 1-5.

The production of (a), (b), (d), (g), (h), (i), (l) and (m) is as mentioned above. In the reaction with (f3), the solvent is not particularly limited, and the reaction is preferably performed in the aforementioned aprotic solvent.

The proportion of charged (f3) relative to (a), (b), (d), (g), (h), (i), (l) or (m) is preferably not less than one equivalent, more preferably 1-10 equivalents. The reaction temperature is preferably −20° C.-100° C., more preferably 0° C.-100° C. The reaction time is preferably 10 min-48 hr, more preferably 30 min-24 hr. When (l) or (m) is used, and a condensation agent such as DCC, EDC and the like may be used appropriately. The thus-obtained acetal form may be purified by the aforementioned purification means, or may be directly used for the next aldehyde-modifying reaction without purification.

The aldehyde form can be produced by hydrolyzing an acetal form in an aqueous solution adjusted to pH 1-4 with an acid such as acetic acid, phosphoric acid, sulfuric acid, hydrochloric acid and the like. The reaction temperature is preferably 0-80° C., more preferably 0-40° C. The reaction time is preferably 10 min-24 hr. more preferably 30 min-10 hr. The produced compound may be purified by the aforementioned purification means.

(Production Method 12: Production Method of (c))

The thiol of (c) can be obtained by reacting compound (j) or (k) with the following compound (c1) and then reducing the resulting compound. The reaction of (j) or (k) with (c1) is performed in the aforementioned aprotic solvent or without solvent. The proportion of (c1) to be used is preferably not less than one equivalent, more preferably within the range of 1-50 equivalents, relative to compound (j) or (k). The reaction temperature is preferably 0-100° C., more preferably 20-60° C. The reaction time is preferably 10 min-48 hr, more preferably 30 min-24 hr. The subsequent reduction is preferably performed using a reducing agent such as dithiothreitol and the like. The produced compound may be purified by the aforementioned purification means.

In addition, the above-mentioned thiol can be obtained by reacting compound (b) with a thio-modifying agent such as thiourea and the like. The production of compound (b) is as mentioned above. The thio-modifying reaction is performed in a solvent such as water, alcohol, acetonitrile and the like or without solvent. The proportion of the thiourea to be used is preferably one or more equivalents, more preferably within the range of 1-50 equivalents, relative to compound (b). The reaction temperature is preferably 0-200° C., more preferably 20° C.-150° C. The reaction time is preferably 10 min-48 hr, more preferably 30 min-24 hr. After the reaction, the produced thiazolium salt is alkali-hydrolyzed to give thiol. The produced compound may be purified by the aforementioned purification means.

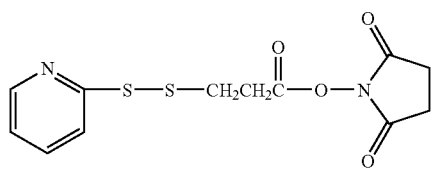

(c1)

An example of the production method according to the method (ii) is shown in the following.
(Production Method 13: Production Method when $X^1$ is (b), (d), (h) or (i))

A polyoxyalkylene derivative having (j) or (a) or (l), which is a reactive functional group with a peptide, on one terminal and a hydroxyl group on the other terminal is reacted with a peptide, and (b), (d), (h) or (i) can be introduced into the hydroxyl group on the polyoxyalkylene chain terminal of the obtained compound according to the method of the production method 7. In this case, the hydroxyl group on the polyoxyalkylene chain terminal may be protected with benzyl group, t-butyl group and the like.

When one terminal of the polyoxyalkylene derivative is (j), a peptide-derived carboxyl group is converted to the activated ester of (a) or (g) according to the method of production method 8, which is then reacted with the polyoxyalkylene derivative of ($j^1$) as shown below under the conditions of production method 2 to give (o1).

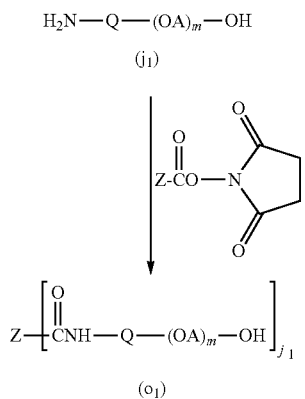

wherein Z is a peptide residue consisting of 2-10 amino acid residues and having one or more amino acid residues having a functional group on the side chain, and Q is an alkylene group, or an alkylene group containing an ether bond, ester bond, urethane bond, amide bond, carbonate bond or secondary amino group.

When one terminal of the polyoxyalkylene derivative is (a) or (l), preferably, a protecting group is bound with the hydroxyl group on the other terminal to give (o2) or (o3), which is subjected to a peptide reaction according to the method of production method 1, followed by deprotection. For example, as shown below, the derivative is reacted with a polyoxyalkylene derivative of (o4) under the conditions of production method 1 and hydrolyzed under acidic conditions to give (o1).

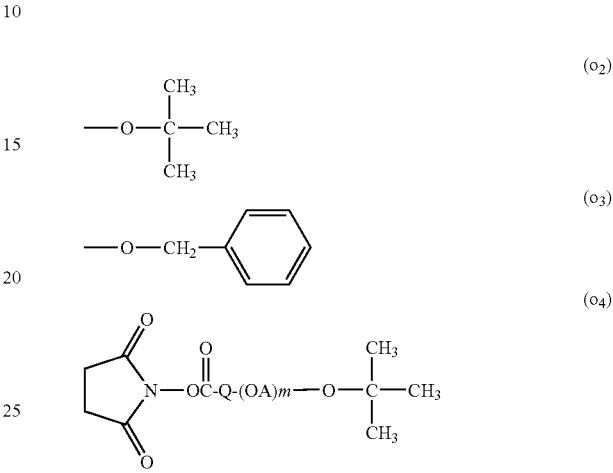

wherein Q is an alkylene group or an alkylene group containing an ether bond, ester bond, urethane bond, amide bond, carbonate bond or secondary amino group.

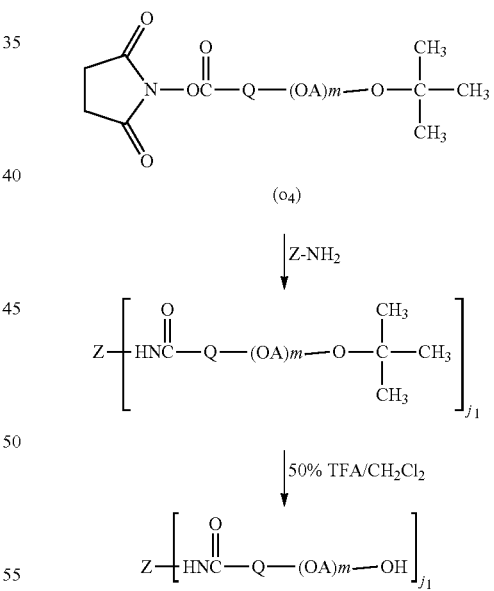

wherein Z is a peptide residue consisting of 2-10 amino acid residues and containing one or more amino acid residues having a functional group on the side chain, and Q is an alkylene group, or an alkylene group containing an ether bond, ester bond, urethane bond, amide bond, carbonate bond or secondary amino group.

While the method of removing (o2) or (o3) is not particularly limited, the benzyl group of (o3) can be produced by the hydrogenation reaction shown below using a palladium-carbon catalyst, hydrogen or hydrogen donor. The amount of palladium is preferably 1-20 wt %. While the reaction solvent is not particularly limited, it is preferably methanol, ethanol, 2-propanol and the like, more preferably methanol. While the hydrogen source is not particularly limited, hydrogen gas, cyclohexene, 2-propanol and the like can be mentioned. The reaction temperature is preferably not more than 60° C. While the reaction time is not particularly limited, when the catalyst amount is high, the reaction is completed in a short time. When the catalyst amount is small, the reaction requires a long time, with preference given to 0.5-8 hr. The obtained compound (o1) may be purified by a purification means such as extraction, recrystallization, adsorption treatment, reprecipitation, column chromatography, supercritical extraction and the like.

As the method of removing the t-butyl group of (o2), the following method can be mentioned. While the reaction solvent is not particularly limited as long as it is stable under acidic conditions, for example, water, acetonitrile, methanol, ethanol, 2-propanol, dioxane, dimethylformamide, toluene, methylene chloride and the like can be used, and a mixed solvent of an organic solvent such as toluene etc. and water and the like can be used without any problem. The acidic condition refers to pH of 4 or below, preferably 2 or below, wherein formic acid, acetic acid, hydrochloric acid, trifluoroacetic acid and the like can be used, the reaction temperature is 0-150° C., preferably 20° C.-100° C., and the reaction time is 10 min-30 hr, preferably 0.5-8 hr. The obtained compound (o1) may be purified in the same manner.

(Production Method 14: Production Method when $X^1$ is (a))

A polyoxyalkylene derivative having (j) or (b) or (d), (h) or (i), which is a reactive functional group with a peptide, on one terminal is reacted with a peptide using a polyoxyalkylene derivative having (1) on the other terminal, and (a) can be introduced into (l) on the polyoxyalkylene chain terminal of the obtained compound according to the method of the production method 8.

When one terminal of the polyoxyalkylene derivative is (j), the peptide-derived carboxyl group is converted to the activated ester of (a) or (g) according to the method of production method 8, which is reacted with the polyoxyalkylene derivative of (11) under the conditions of production method 2 to give a terminal carboxyl form (12). In addition, when one terminal of the polyoxyalkylene derivative is (b), it is reacted with the peptide-derived amino group according to the method of production method 4 to give a terminal carboxyl form (13). Moreover, when one terminal of the polyoxyalkylene derivative is (d), (h) or (i), terminal carboxyl form (14) can be obtained by reacting with a peptide-derived amino group according to the method of production method 8.

The obtained (12), (13) or (14) is processed according to the method of production method 8 to give (a1), (a2) or (a3) wherein $X^1$ is (a). An example of (a3) is shown below.

wherein $Q_1$ and $Q_2$ are each independently an alkylene group, or an alkylene group containing an ether bond, ester bond, urethane bond, amide bond, carbonate bond or secondary amino group.

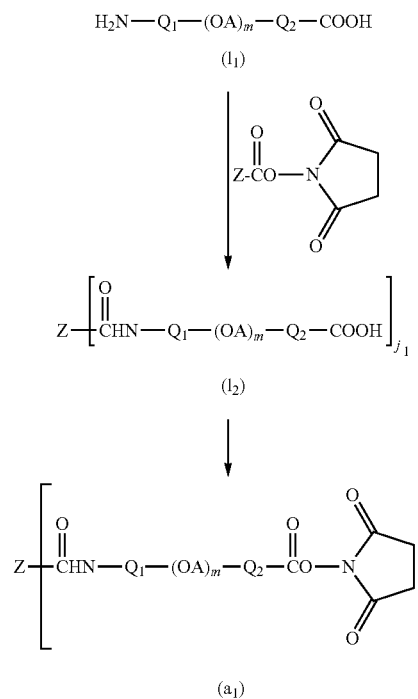

wherein Z is a peptide residue consisting of 2-10 amino acid residues and containing one or more amino acid residues having a functional group on the side chain, and $Q_1$ and $Q_2$ are each an alkylene group, or an alkylene group containing an ether bond, ester bond, urethane bond, amide bond, carbonate bond or secondary amino group.

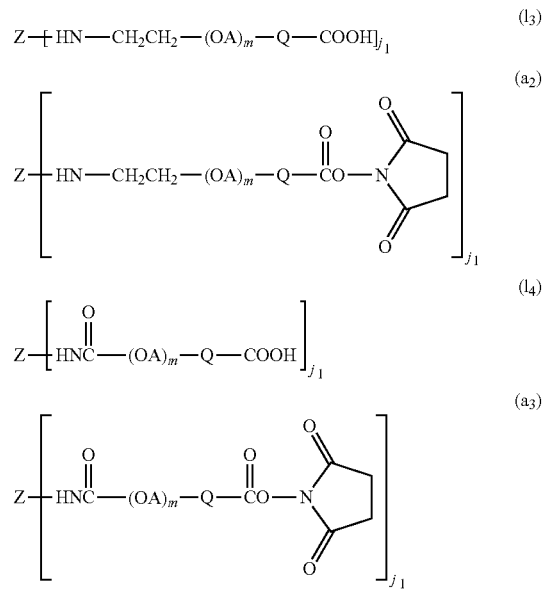

wherein Z is a peptide residue consisting of 2-10 amino acid residues and containing one or more amino acid residues having a functional group on the side chain, and Q is an alkylene group, or an alkylene group containing an ether bond, ester bond, urethane bond, amide bond, carbonate bond or secondary amino group.

(Production Method 15: Production Method when $X^1$ is (j))

A polyalkylene derivative having (a), (d), (h) or (i), which is a reactive functional group with a peptide, on one terminal and (j2) wherein (j) is bonded with a protecting group, on the other terminal is reacted with a peptide and thereafter deprotected to give (j).

When one terminal of a polyoxyalkylene derivative is (a), (j3) having (j2) on the other terminal is reacted with a peptide-derived amino group according to the method of production method 1. When one terminal of a polyoxyalkylene derivative is (d), (h) or (i), it is reacted with a peptide-derived amino group according to the method of production method 8. After each reaction, (j) can be obtained in the same manner as in production method 13 by a catalytic reduction using a palladium catalyst, an acid treatment or deprotection by a method using hydrogen bromide/acetic acid or hydrogen fluoride in the same manner as in production method 13.

(j2)

wherein D is a benzyl group, a t-butyl group, a p-nitrobenzyl group, a p-methoxybenzyl group, a 2-phenylisopropyl group, a 9-fluorenylmethyl group, a methylsulfonylethyl group or a 2,2,2-trichloroethyl group, and Q is an alkylene group, or an alkylene group containing an ether bond, ester bond, urethane bond, amide bond, carbonate bond or secondary amino group.

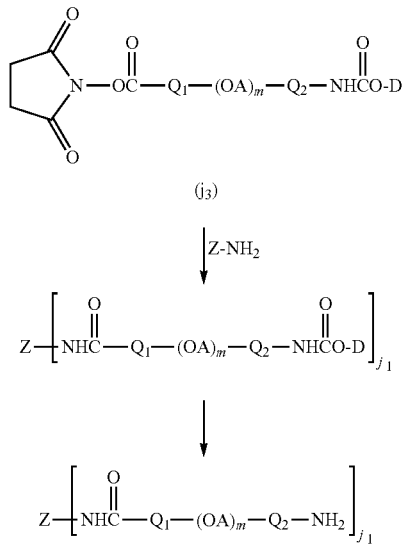

wherein D is a benzyl group, a t-butyl group, a p-nitrobenzyl group, a p-methoxybenzyl group, a 2-phenylisopropyl group, a 9-fluorenylmethyl group, a methylsulfonylethyl group or a 2,2,2-trichloroethyl group, and $Q_1$ and $Q_2$ are each an alkylene group, or an alkylene group containing an ether bond, ester bond, urethane bond, amide bond, carbonate bond or secondary amino group.

(Production Method 16: Production Method when $X^1$ is (e))

By reacting a polyoxyalkylene derivative (e2) having (e), which is a reactive functional group with a peptide, on one terminal and (a) on the other terminal with the amino group of a peptide according to the method of production method 1, or by reacting a polyoxyalkylene derivative having (d), (h), (i) on the other terminal with the amino group of a peptide according to the method of production method 3, (e) can be introduced.

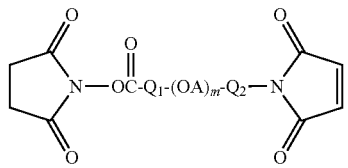
(e2)

wherein $Q_1$ and $Q_2$ are as defined above.

(Production Method 17: Production Method when $X^1$ is (f))

Acetal group can be introduced by reacting a polyoxyalkylene derivative having acetal introduced into one terminal by the method described in production method 11, and having (a) at the other terminal, with the amino group of a peptide according to the method of production method 1, or by reacting a polyoxyalkylene derivative having (d), (h) or (i) on the other terminal with the amino group of a peptide according to the method of production method 3. In addition, by hydrolysis by the method described in production method 11, (f) can be obtained.

(Production Method 18: Production Method when $X^1$ is (c))

When a polyoxyalkylene derivative having (c), which is a reactive functional group with a peptide, on one terminal and (j) on the other terminal is used, a peptide-derived carboxyl group is converted to an activated ester of (a) or (g) according to the method of production method 8, which is reacted with (j) of the polyalkylene derivative under the conditions of production method 2 to give (c).

An example of the production method according to the method (iii) is shown in the following.

The reaction of amino acid and polyoxyalkylene compound can be performed in the same manner as described in the method (i). The reaction of amino acid and amino acid is not particularly limited and a known method can be employed as long as it can produce an amide bond by condensation, with dehydration, of the amino group of one amino acid and the carboxyl group of the other amino acid. The reaction of a peptide wherein two or more amino acid residues are bonded with amino acid can also be performed in the same manner as described for the amino acids. In the synthesis steps, the amino group, carboxyl group and other functional groups on the amino acid side chain can be protected by the protecting groups described in Nobuo Izumiya, et al.: Peptide Gosei-no-Kiso to Jikken (Basics and experiments of peptide synthesis), published by Maruzen Co. (1975).

EXAMPLES

The present invention is explained in detail in the following by referring to Examples, which are not to be construed as limitative.

In the following, each amino acid residue is shown by the following abbreviations.

Glycine: Gly, glutamic acid: Glu, lysin: Lys, and cysteine: Cys.

Example 1

Synthesis of methylpolyoxyethylenecarbamyl-Gly-Lys(-methylpolyoxyethylenecarbamyl)-Gly-Gly-Gly-succinate ester <MeO-PEG2000-Gly-Lys(-PEG2000-OMe)-Gly-Gly-Gly-NHS>

(1) Synthesis of methylpolyoxyethylenecarbamyl-Gly-Lys(-methylpolyoxyethylenecarbamyl)-Gly-Gly-Gly <MeO-PEG2000-Gly-Lys(—PEG2000-OMe)-Gly-Gly-Gly >

Methoxy polyethylene glycol-p-nitrophenylcarbonate (SUNBRIGHT MENP-20H, weight-average molecular weight 2000, manufactured by NOF Corporation, formula (3), 12 g, 6 mmol) was dissolved in acetonitrile (40 mL). A solution of Gly-Lys-Gly-Gly-Gly (SEQ ID NO: 1, 0.75 g, 2 mmol) in water (10 mL) was added to the solution, and the mixture was stirred. Triethylamine (0.5 g, 0.5 mmol) was added, and the mixture was stirred at room temperature for 3 hr. After completion of the reaction, an insoluble material was removed by filtration, and the solvent was removed under reduced pressure in an evaporator. Then, ethyl acetate (50 mL) was added, and the mixture was dissolved. Sodium sulfate was added, and the mixture was stirred, filtrated and dehydrated. Hexane (100 mL) was added to the filtrate, and the mixture was cooled to 10° C. or below and filtrated to give crude crystals. The crude crystals were dissolved in ethyl acetate (50 mL), Kyoward#2000 (0.05 g), Kyoward#700 (0.1 g) were added as adsorbents, and the mixture was stirred at 60° C. for 1 hr. The adsorbents were filtered off, hexane (100 mL) was added, and the mixture was cooled to allow crystallization. The obtained crystals were objected to recrystallization by addition of ethyl acetate (200 mL), and the crystals were collected by filtration and dried to give the object compound (6.2 g, theoretical yield 70%).

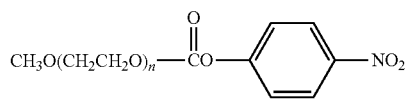

(3)

(2) Synthesis of (methylpolyoxyethylenecarbamyl)-Gly-Lys(-methy polyoxyethylenecarbamyl)-Gly-Gly-Gly-succinate ester <MeO-PEG2000-Gly-Lys(-PEG2000-OMe)-Gly-Gly-Gly-NHS>

The crystals obtained in (1) were dissolved in chloroform (20 mL), N-hydroxysuccinimide (0.2 g, 1.7 mmol) was added, and the mixture was stirred for 30 min. Dicyclohexylcarbodiimide (DCC, 0.6 g, 2.7 mmol) was added, and the mixture was stirred at room temperature for 2 hr. After the reaction, the resulting dicyclohexylurea (DCU) was filtered off, and the solvent was removed under reduced pressure in an evaporator. Ethyl acetate (200 mL) was added, and the mixture was dissolved by heating. After cooling to room temperature, hexane (200 mL) was added to allow crystallization. The crystals were collected by filtration. Similar crystallization was further performed twice, and the obtained crystals were dried to give MeO-PEG2000-Gly-Lys(-PEG2000-OMe)-Gly-Gly-Gly-NHS as crystals (5.1 g).

The progress of the reaction and identification of the resultant product were performed by thin layer chromatography (TLC) using a silica gel plate. Using a mixed solvent having a chloroform to methanol mixing ratio (volume ratio) of 85:15 as a developing solvent, color was developed by iodine vapor, and the substance was identified based on the comparison of Rf value of the standard substance. The reaction terminal point was confirmed by the conversion of the spot of methoxy polyethylene glycol-p-nitrophenylcarbonate detected at Rf value of around 0.7-0.8 and the spot of Gly-Lys-Gly-Gly-Gly (SEQ ID NO: 1) detected at Rf value of around 0.1 to the spot detected around Rf value of 0.3-0.4 by the above-mentioned TLC. Regarding the identification of the resultant product, the presence of methylpolyoxyethylene chain, peptide chain and succinimide ester was confirmed by the fact that methylpolyoxyethylene-derived terminal methyl group, polyoxyethylene-derived ethylene group, peptide-derived methylene group and succinimide ester-derived ethylene group were detected by $^1$H-NMR at δ: around 3.3 ppm, δ: around 3.5 ppm, δ: around 1.5 ppm, and δ: around 2.8 ppm, respectively. In addition, integration value A derived from the ethylene group of polyoxyethylene at δ: around 3.5 ppm was measured when the integration value of the peaks at δ: around 3.3 ppm was 6 (derived from methyl terminals of two methylpolyoxyethylenes), and the molecular weight of polyoxyethylene in the resultant product was calculated by the following calculation. The calculated molecular weight was 4235.

Since the value obtained by the number of repeats of oxyethylene group molecule multiplied by 44 is the molecular weight of polyoxyethylene, and the number of proton contained in one molecule of oxyethylene group is 4, the integration value A×44/4 is the molecular weight of polyoxyethylene chain. δ (ppm): 3.38 (6H, s, —CH$_3$), 3.40-3.80 (385H, m, —NHOCO(CH$_2$CH$_2$O)$_m$CH$_3$)

For $^1$H-NMR analysis, JNM-ECP400 manufactured by JEOL Ltd. was used. The following measurement was performed in the same manner. $^1$H-NMR (CDCl$_3$, internal standard TMS)

The production scheme of Example 1 is shown below.

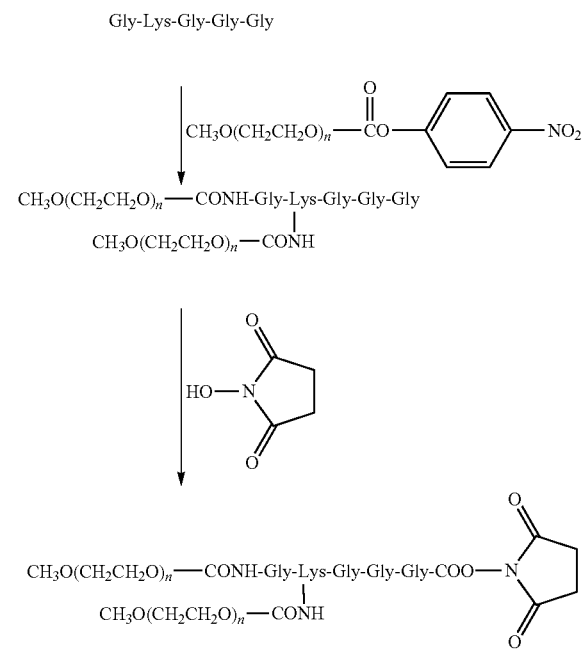

Example 2

Synthesis of methylpolyoxyethylenecarbamyl-Cys(-methylpolyoxyethylene-thiosuccinimide)-Gly-Gly-succinimide ester <MeO-PEG5000-Cys(-PEG2000-OMe)-Gly-Gly-NHS>

(1) Synthesis of methylpolyoxyethylenecarbamyl-Cys <MeO-PEG5000-Cys>

To L-cystine (manufactured by Ajinomoto Takara Co., Inc., 2.5 g, 10.5 mmol) was added borate buffer (0.1 M, pH 9.5, 150 mL), and the mixture was stirred until complete dissolution. A solution of methoxy polyethylene glycol-p-nitrophenylcarbonate (trade name: SUNBRIGHT MENP-50H, average molecular weight 5000, manufactured by NOF Corporation) (75 g, 15 mmol) in water (100 mL) was added to the L-cystine solution, and the mixture was reacted maintaining the pH at 9.5 at room temperature for 2 hr. After completion of the reaction, the reaction mixture was adjusted to pH 5.5 with dilute hydrochloric acid, and cooled to 2° C. Then, the insoluble material was filtered off, and the filtrate was dialyzed 5 times with 2 L of ion exchanged water using a dialysis tube (fraction molecular weight 3500 Da). After the completion of dialysis, the solution was adjusted to pH 7.5, cooled to 2° C. and reduced by addition of 1,4-dithiothreitol (2.8 g). After the reduction, the reaction solution was dialyzed against 1.5% aqueous acetic acid solution and freeze-dried to give methylpolyoxyethylenecarbamyl-cysteine as crystals (61 g).

(2) Synthesis of methylpolyoxyethylenecarbamyl-Cys(-methylpolyoxyethylene-thiosuccinimide) <MeO-PEG5000-Cys(-PEG2000-OMe)>

Methylpolyoxyethylenecarbamyl-cysteine (5.1 g, 1 mmol) obtained in (1) was dissolved in physiological-buffered saline (PBS, 50 mL), α-[3-(3-maleimide-1-oxopropyl)amino]propyl-O-methoxy, polyoxyethylene (trade name: SUNBRIGHT ME-020MA, average molecular weight 2000, manufactured by NOF Corporation, following formula (4), 2.4 g, 1.2 mmol) was added, and the mixture was reacted at room temperature for 8 hr. After the reaction, sodium chloride was added and dissolved therein to give a 20% w/w aqueous solution. After extraction with chloroform (50 mL), anhydrous magnesium sulfate was added, and the mixture was stirred, filtrated and dehydrated. The solvent was removed under reduced pressure in an evaporator, and the residue was re-dissolved in ethyl acetate. Then, hexane was added to allow crystallization, and the crystals were collected by filtration to give methylpolyoxyethylenecarbamyl-Cys(-methylpolyoxyethylene-thiosuccinimide) as crystals (5.2 g, theoretical yield 73%).

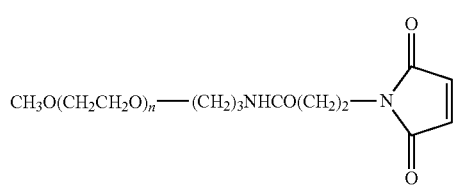

(4)

(3) Synthesis of methylpolyoxyethylenecarbamyl-Cys (-methylpolyoxyethylene-thiosuccinimide) succinimide ester <MeO-PEG5000-Cys (-PEG2000-OMe)-NHS>

Methylpolyoxyethylenecarbamyl-cysteine (methylpolyoxyethylene thiosuccinimide) obtained in (2) (4.2 g, 0.58 mmol) was dissolved in chloroform (80 mL), N-hydroxysuccinimide (0.1 g, 0.87 mmol) was added, and the mixture was stirred for 30 min. DCC (0.24 g, 1.16 mmol) was added, and the mixture was stirred at room temperature for 2 hr. After the reaction, the resulting DCU was filtered off, and solvent was removed under reduced pressure in an evaporator. Ethyl acetate (100 mL) was added, and the mixture was dissolved by heating. After the solution was allowed to cool to room temperature, hexane (100 mL) was added to allow crystallization, and the crystals were collected by filtration. Similar crystallization was further performed twice, and the crystals were dried to give methylpolyoxyethylenecarbamyl-Cys (-methylpolyoxyethylene-thiosuccinimide) succinimide ester as crystals (3.2 g).

(4) Synthesis of methylpolyoxyethylenecarbamyl-Cys (-methylpolyoxyethylene-thiosuccinimide)-Gly-Gly<MeO-PEG5000-Cys-Gly-Gly>

Gly-Gly (53 mg, 0.4 mmol) was added to dimethylformamide (1 mL), and the mixture was stirred. Triethylamine (65 mg, 0.64 mmol) was further added. A solution of the crystals obtained in (3) (3 g, 0.4 mmol) in acetonitrile (10 mL) was added dropwise to this solution, and the mixture was reacted at room temperature for 4 hr. After the reaction, the reaction solution was dehydrated by concentration, ethyl acetate (100 mL) was added, and the mixture was dissolved by heating. After the solution was allowed to cool to room temperature, the insoluble material was filtered off. Hexane (100 mL) was added to allow crystallization, and the crystals were collected by filtration. Similar crystallization was further performed twice, and the obtained crystals were dried to give methylpolyoxyethylenecarbamyl-Cys(-methylpolyoxyethylene thiosuccinimide)-Gly-Gly as crystals (2.2 g).

(5) Synthesis of methylpolyoxyethylenecarbamyl-Cys(-methylpolyoxyethylene-thiosuccinimide)-Gly-Gly-succinimide ester The crystals obtained in (4) were dissolved in chloroform and, in the same manner as in Example 1 (2), methylpolyoxyethylenecarbamyl-Cys(-methylpolyoxyethylene-thiosuccinimide)-Gly-Gly-succinimide ester, wherein the carboxyl group at the carboxyl-terminal of glycine was succinimide ester, was obtained as crystals (1.15 g).

The progress of the reaction and identification of the resultant product were performed in the same manner as in Example 1, and conversion of the spot of a methylpolyoxyethylene compound detected at Rf value of around 0.7-0.8 and the spot of peptide detected at Rf value of around 0.1 to the spot detected at Rf value of around 0.3-0.4 was confirmed by thin layer chromatography. For confirmation of the resultant product, the presence of methylpolyoxyethylene chain, peptide chain and succinimide ester was confirmed by $^1$H-NMR. The molecular weight of polyoxyethylene in the resultant product as determined by $^1$H-NMR was 7230.

δ (ppm): 3.38 (6H, s, —CH$_3$), 3.40-3.80 (657H, m, —NHOCO(CH$_2$CH$_2$O)$_m$CH$_3$)

For $^1$H-NMR analysis, JNM-ECP400 manufactured by JEOL Ltd. was used. $^1$H-NMR (CDCl$_3$, internal standard TMS)

The production scheme of Example 2 is shown below.
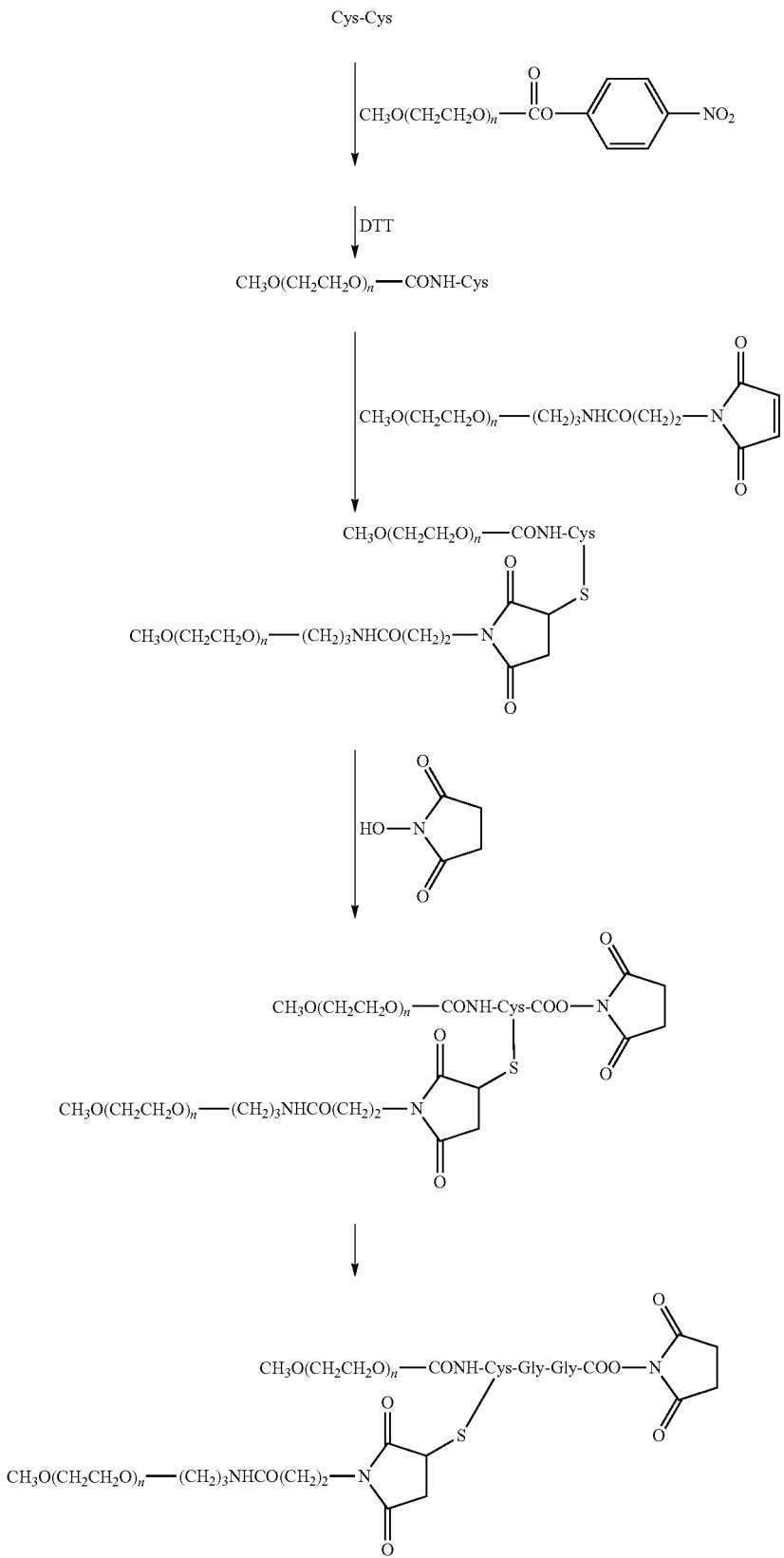

Example 3

Synthesis of methylpolyoxyethylenecarbamyl-Gly-Lys(-methylpolyoxyethylenecarbamyl)-Gly-Gly-amide propylpolyoxyethylene-carbonylimidazole <MeO-PEG20000-Gly-Lys(-PEG20000-OMe)-Gly-Gly-PEG2000-CI>

(1) Synthesis of methylpolyoxyethylenecarbamyl-Gly-Lys(methylpolyoxyethylenecarbamyl)-Gly-Gly<MeO-PEG20000-Gly-Lys(—PEG20000-OMe)-Gly-Gly>

Using methoxy polyethylene glycol-p-nitrophenylcarbonate (trade name: SUNBRIGHT MENP-20T, average molecular weight 20000, manufactured by NOF Corporation, 8 g, 0.4 mmol) and Gly-Lys-Gly-Gly (SEQ ID NO: 2, 50 mg, 0.16 mmol) and by the reaction and purification in the same manner as in Example 1, methylpolyoxyethylenecarbamyl-Gly-Lys(-methylpolyoxyethylenecarbamyl)-Gly-Gly (5.2 g) was obtained.

(2) Synthesis of methylpolyoxyethylenecarbamyl-Gly-Lys(-methylpolyoxyethylenecarbamyl)-Gly-Gly-succinimide ester <MeO-PEG20000-Gly-Lys(-PEG20000-OMe)-Gly-Gly-NHS>

Methylpolyoxyethylenecarbamyl-Gly-Lys(-methylpolyoxyethylenecarbamyl)-Gly-Gly (1.5 g, 0.04 mmol) obtained above was dissolved in chloroform (20 mL) and, in the same manner as in Example 2 (3), the carboxy-terminal carboxyl group of peptide was converted to succinimide ester to give crystals.

(3) Synthesis of methylpolyoxyethylenecarbamyl-Gly-Lys(-methylpolyoxyethylenecarbamyl)-Gly-Gly-amidepropylpolyoxyethylene<MeO-PEG20000-Gly-Lys(-PEG20000-OMe)-Gly-Gly-PEG2000-OH>

The crystals of methylpolyoxyethylenecarbamyl-Gly-Lys(-methylpolyoxyethylenecarbamyl)-Gly-Gly-succinimide ester obtained in (2) were dissolved in chloroform (20 mL), a solution of α-aminopropyl-ω-hydroxy-polyoxyethylene (trade name: SUNBRIGHT HO-020PA, average molecular weight 2000, manufactured by NOF Corporation, following formula (5), 0.5 g) in dimethylformamide (5 mL) was added, and the mixture was stirred. Triethylamine (20 mg) was further added, and the mixture was reacted at 40° C. for 10 hr. After the reaction, the reaction solution was purified in the same manner as in the above-mentioned (2) to give crystals (1.03 g).

$$NH_2(CH_2)_3O(CH_2CH_2O)_nH \quad (5)$$

(4) Synthesis of methylpolyoxyethylenecarbamyl-Gly-Lys(-methylpolyoxyethylenecarbamyl)-Gly-Gly-amide propylpolyoxyethylene-carbonylimidazole <MeO-PEG20000-Gly-Lys(—PEG20000-OMe)-Gly-Gly-PEG2000-CI>

The crystals obtained in (3) were dissolved in chloroform (10 mL), and triethylamine (20 mg) was added. Carbonyldiimidazole (10 mg) was further added, and the mixture was reacted at 50° C. for 4 hr. The reaction solution was filtrated, and the solvent was removed under reduced pressure in an evaporator. Ethyl acetate (5 mL) was added, the mixture was dissolved, and the solution was cooled in ice water. Hexane (10 mL) was further added, and the mixture was filtrated to give crystals. Similar crystallization operation (twice) gave crystals (870 mg).

The progress of the reaction and identification of the resultant product were performed in the same manner as in Example 1, and conversion of the spot of a methylpolyoxyethylene compound detected at Rf value of around 0.7-0.8 and the spot of peptide detected at Rf value of around 0.1 to the spot detected at Rf value of around 0.3-0.4 was confirmed by thin layer chromatography. For confirmation of the resultant product, the presence of methylpolyoxyethylene chain, peptide chain and carbonylimidazole (δ: around 7.1 ppm, δ: around 7.4 ppm and δ: around 8.1 ppm) was confirmed by $^1$H-NMR. The molecular weight of polyoxyethylene in the resultant product as determined by $^1$H-NMR was 43440.

δ (ppm): 3.38 (6H, s, —CH$_3$), 3.40-3.80 (3945H, m, —NHOCO(CH$_2$CH$_2$O)$_m$CH$_3$, —NH(CH$_2$)(0)(CH$_2$CH$_2$O)$_m$CO—)

For $^1$H-NMR analysis, JNM-ECP400 manufactured by JEOL Ltd. was used. $^1$H-NMR (CDCl$_3$, internal standard TMS)

The production scheme of Example 3 is shown below.

Gly-Lys-Gly-Gly

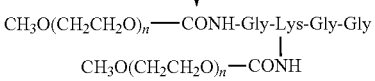

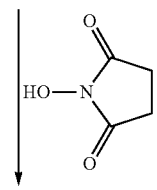

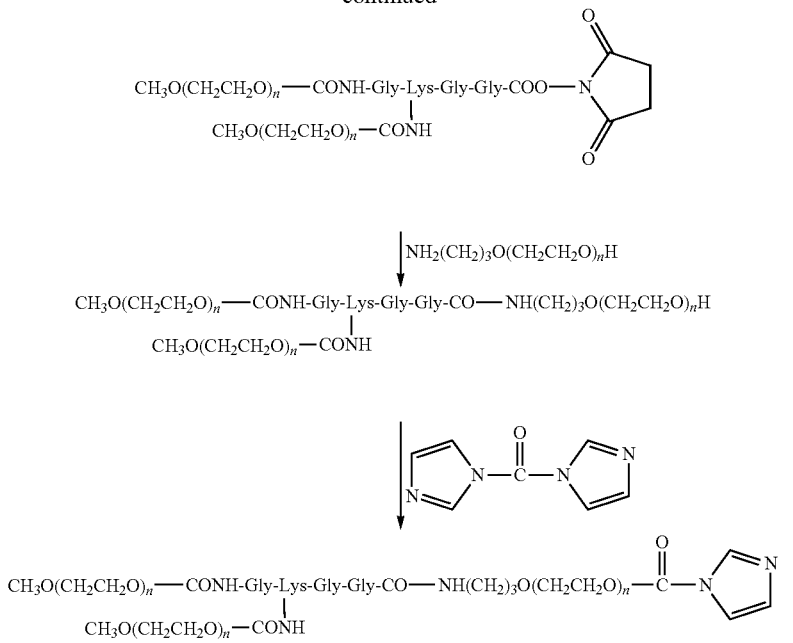

Example 4

Synthesis of methylpolyoxyethylenecarbamyl-Gly-Gly-Glu(-propylaldehyde-polyoxyethyleneoxypropylamide)-Gly-propylaldehyde-polyoxyethyleneoxypropylamide <MeO-PEG30000-Gly-Gly-Glu(-PEG5000-ALD)-Gly-PEG5000-ALD>

(1) Synthesis of methylpolyoxyethylenecarbamyl-Gly-Gly-Glu-Gly<MeO-PEG30000-Gly-Gly-Glu-Gly>

Methoxy polyethylene glycol-p-nitrophenylcarbonate (SUNBRIGHT MENP-30T, weight-average molecular weight 30000, manufactured by NOF Corporation, 3 g, 0.1 mmol) was dissolved in acetonitrile (30 mL), a solution of Gly-Gly-Glu-Gly (SEQ ID NO: 3, 20 mg, 0.062 mmol) in water (1 mL) was added to this solution and, in the same manner as in Example 1, methylpolyoxyethylenecarbamyl-Gly-Gly-Glu-Gly was obtained as crystals (1.52 g).

(2) Synthesis of methylpolyoxyethylenecarbamyl-Gly-Gly-Glu(-(diethoxy)propyl-polyoxyethyleneoxypropylamide)-Gly-(diethoxy)propylpolyoxyethyleneoxypropylamide <MeO-PEG30000-Gly-Gly-Glu(-PEG5000-DEP)-Gly-PEG5000-DEP>

The crystals obtained in (1) were dissolved in chloroform and, in the same manner as in Example 2 (3), crystals wherein the carboxyl group was succinimide ester were obtained. The obtained crystals were dissolved in chloroform (10 mL), α-aminopropyl-ω-3,3-diethoxypropyloxy, polyoxyethylene (weight-average molecular weight 5000, following formula (6), 600 mg, 0.12 mmol) was added, and the mixture was reacted at 40° C. for 8 hr. After the reaction, the insoluble material was filtered off, and the solvent was removed under reduced pressure in an evaporator. Ethyl acetate and hexane were added to allow crystallization, and the crystals were purified to give crystals (1.15 g).

$$NH_2(CH_2)_3O(CH_2CH_2O)_nCH_2CH_2CH\begin{matrix}OCH_2CH_3\\OCH_2CH_3\end{matrix} \quad (6)$$

(3) Synthesis of methylpolyoxyethylenecarbamyl-Gly-Gly-Glu(-propylaldehyde-polyoxyethyleneoxypropylamide)-Gly-propylaldehydepolyoxyethyleneoxypropylamide <MeO-PEG30000-Gly-Gly-Glu(—PEG5000-ALD)-Gly-PEG5000-ALD>

The crystals obtained in (2) were dissolved in water (50 mL), and the solution was adjusted to pH 2 with phosphoric acid and stirred at room temperature for 2 hr. Then, sodium chloride (10 g) was added and dissolved therein. The mixture was adjusted to pH 7.0 with 30% aqueous sodium hydroxide solution, and extracted 3 times with chloroform. The obtained chloroform layer was dried over sodium sulfate and filtrated. Chloroform was evaporated, and the residue was concentrated. Toluene (5 mL) and ethyl acetate (5 mL) were added to the concentrated solution, and the mixture was dissolved by heating. Hexane (20 mL) was added to allow crystallization, and the crystals were collected by filtration. The obtained crystals were dried to give methylpolyoxyethylenecarbamyl-Gly-Gly-Glu(-propylaldehyde-polyoxyethyleneoxypropylamide)-Gly-(propylaldehydepolyoxyethyleneoxypropylamide), wherein the terminal was aldehyde (0.95 g).

The progress of the reaction and identification of the resultant product were performed in the same manner as in Example 1, and conversion of the spot of a methylpolyoxyethylene compound detected at Rf value of around 0.7-0.8 and the spot of peptide detected at Rf value of around 0.1 to the spot detected at Rf value of around 0.3-0.4 was confirmed by thin layer chromatography. For confirmation of the resultant product, the presence of methylpolyoxyethylene chain, peptide chain and aldehyde (δ: around 9.8 ppm) was confirmed by ¹H-NMR. The molecular weight of polyoxyethylene in the resultant product as determined by ¹H-NMR was 421000.

δ (ppm): 3.38 (3H, s, —CH₃), 3.40-3.80 (3827H, m, —NHOCO(CH₂CH₂O)$_m$CH₃, —O(CH₂CH₂O)$_m$CH₂H₂CHO)

For ¹H-NMR analysis, JNM-ECP400 manufactured by JEOL Ltd. was used. ¹H-NMR (CDCl₃, internal standard TMS)

The production scheme of Example 4 is shown below.

(3-maleimide-1-oxopropyl)amino]propyl-ω-methoxy, polyoxyethylene (SUNBRIGHT ME-200MA, weight-average molecular weight 20000, manufactured by NOF Corporation) (1 g, 0.05 mmol) was added to the solution in the form of a powder, and the mixture was reacted at 4° C. for 4 hr. The reaction mixture was subjected to the following column purification, and the obtained aqueous solution was extracted with chloroform, the obtained chloroform layer was concentrated in an evaporator. Ethyl acetate and hexane were added to allow crystallization to give crystals (520 mg).

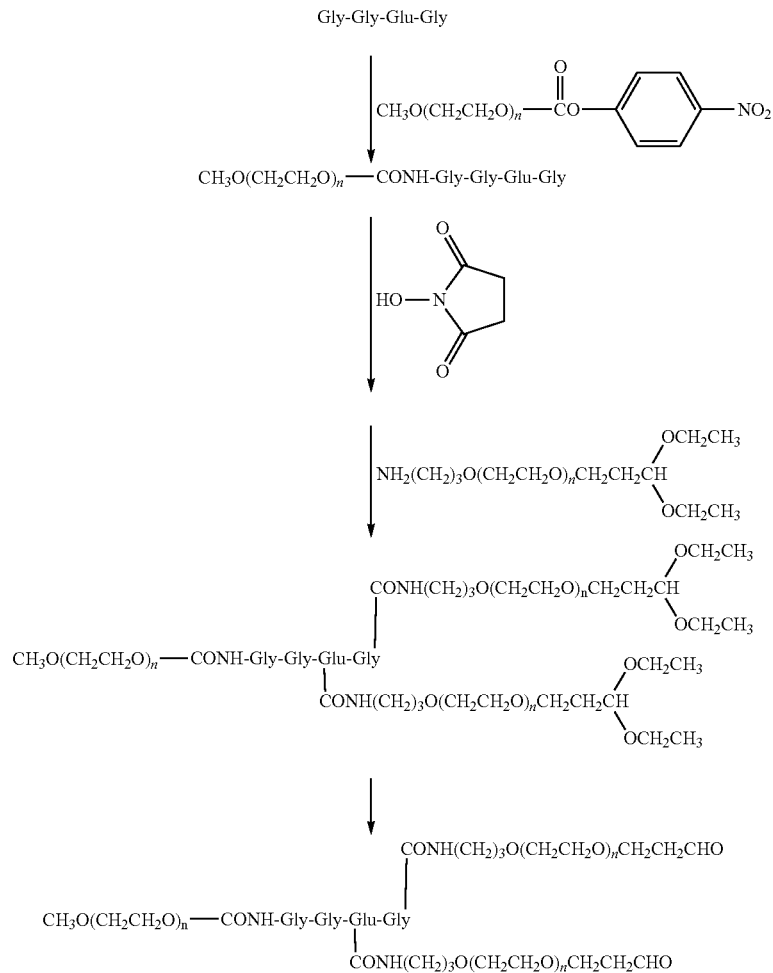

Example 5

Synthesis of maleimidepropylamidepropyl-polyoxyethyleneheptylamide-Gly-Lys(-maleimidepropylamidepropyl-polyoxyethyleneheptylamide)-Cys(-methylpolyoxyethylene-thiosuccinimide)-Gly-succinimide ester <MAL-PEG5000-Gly-Lys(-PEG5000-MAL)-Cys(-PEG20000-MeO)-Gly-NHS>

(1) Synthesis of Gly-Lys-Cys(-methylpolyoxyethylene-thiosuccinimide)-Gly<Gly-Lys-Cys(-PEG20000-MeO)-Gly>

Gly-Lys-Cys-Gly (12 mg, 0.033 mmol) was adjusted to 4 mg/mL with 0.1 N sodium phosphate buffer (pH 6.4), α-[3-(3-maleimide-1-oxopropyl)amino]propyl-ω-methoxy, polyresin: SP Sepharose FF
solvent: 20 mM Tris-HCl (pH 8.2)/1 M NaCl/20 mM Tris-HCl (pH 8.2)

(2) Synthesis of maleimidepropylamidepropyl-polyoxyethyleneheptylamide-Gly-Lys(-maleimidepropylamidepropyl-polyoxyethyleneheptylamide)-Cys(-methylpolyoxyethylene-thiosuccinimide)-Gly<MAL-PEG5000-Gly-Lys(-PEG5000-MAL)-Cys(-PEG20000-MeO)-Gly>

The crystals obtained in (1) were dissolved in chloroform (10 mL), triethylamine (2.5 mg, 0.025 mmol) was added, and α-[3-(3-maleimide-1-oxopropyl)amino]propyl-ω-succinimidylcarboxypentyloxy, polyoxyethylene (weight-average molecular weight 5000, following formula (7), 0.3 g, 0.06 mmol) was added in the form of a powder, and the mixture was stirred at 40° C. for 5 hr. After the reaction, the reaction solution was filtrated, and ethyl acetate and hexane were added to allow crystallization to give crystals (0.51 g).

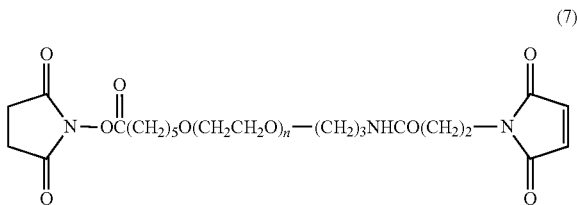

(7)

(3) Synthesis of maleimidepropylamidepropyl-polyoxyethyleneheptylamide-Gly-Lys(-maleimidepropylamidepropyl-polyoxyethyleneheptylamide)-Cys(-methylpolyoxyethylene-thiosuccinimide)-glycyl-succinimide ester <MAL-PEG5000-Gly-Lys(-PEG5000-MAL)-Cys(-PEG20000-MeO)-Gly-NHS>

The crystals obtained in (2) were dissolved in chloroform and, in the same manner as in Example 2 (3), maleimidepropylamidepropyl-polyoxyethyleneheptylamide-Gly-Lys(-maleimidepropylamidepropyl-polyoxyethyleneheptylamide)-Cys (-methylpolyoxyethylene-thiosuccinimide)-Gly-succinimide ester, wherein carboxyl group was succinimide ester, was obtained as crystals (0.4 g).

The progress of the reaction and identification of the resultant product were performed in the same manner as in Example 1, and conversion of the spot of a methylpolyoxyethylene compound detected at Rf value of around 0.7-0.8 and the spot of peptide detected at Rf value of around 0.1 to the spot detected at Rf value of around 0.3-0.4 was confirmed by thin layer chromatography. For confirmation of the resultant product, methylpolyoxyethylene chain, peptide chain, succinimide ester and maleimide group (δ: around 6.8 ppm) were confirmed by $^1$H-NMR. The molecular weight of polyoxyethylene in the resultant product as determined by $^1$H-NMR was 32400.

For $^1$H-NMR analysis, JNM-ECP400 manufactured by JEOL Ltd. was used. $^1$H-NMR (CDCl$_3$, internal standard TMS)

The production scheme of Example 5 is shown below.

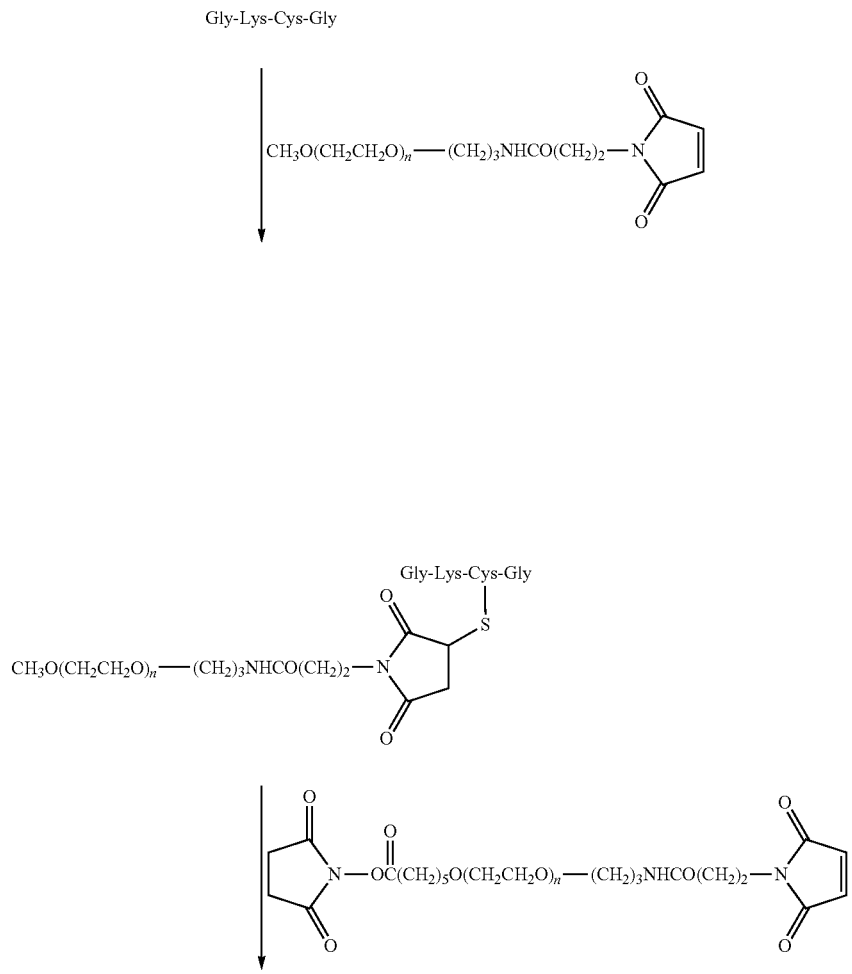

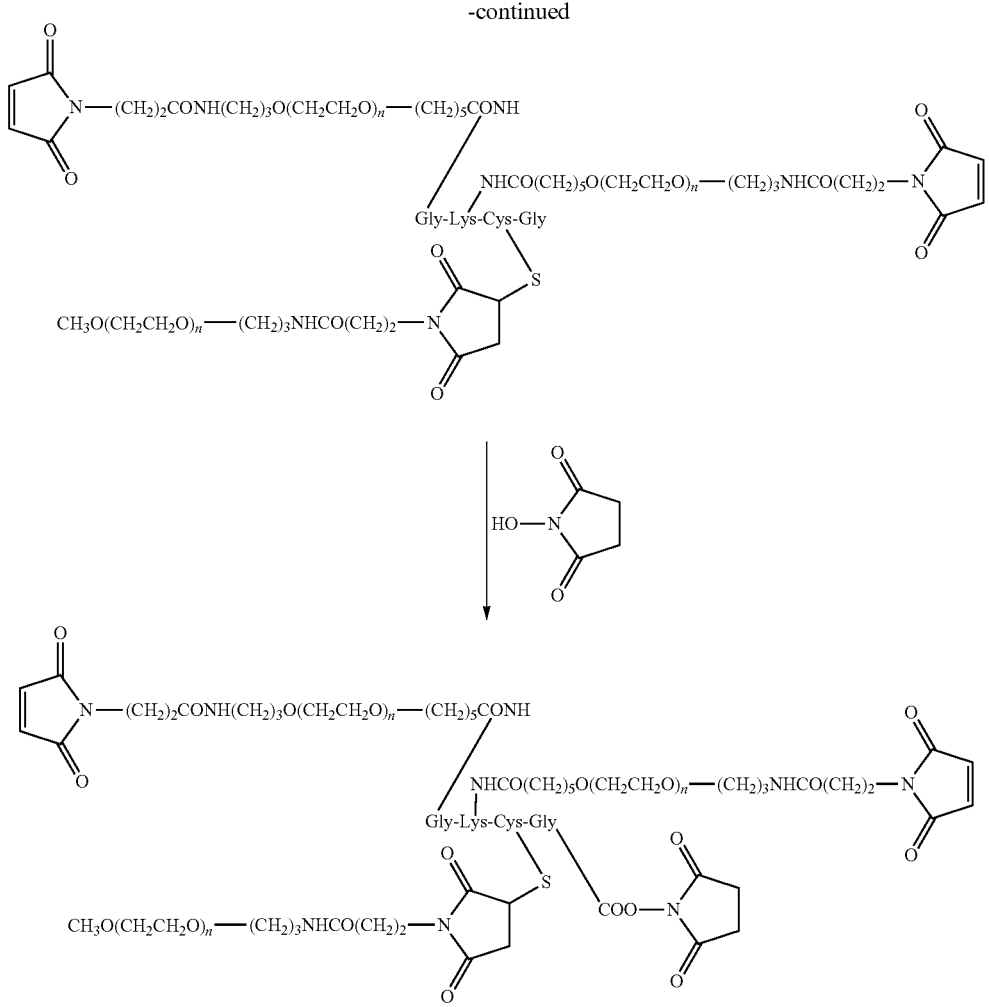

Example 6

Synthesis of maleimidepropylamidepropyl-polyoxy-ethylenecarbamyl-{Lys(maleimidepropylamidepropyl-polyoxyethylenecarbamyl)}$_4$-succinimide ester <MAL-PEG3400-{Lys(-PEG3400-MAL)}$_4$-NHS>

(1) Synthesis of t-butyloxycarbonyl-aminopropyl-polyoxyethylenecarbamyl-{Lys(t-butyloxycarbonyl-aminopropyl-polyoxyethylenecarbamyl)}$_4$<Boc-PEG3400-{Lys (-PEG3400-Boc)}$_4$> t-Butyloxycarbonyl (Boc)-aminopropyl-polyoxyethylene-p-nitrophenylcarbonate (weight-average molecular weight 3400, following formula (8), 2 g, 0.6 mmol) was dissolved in acetonitrile (10 mL), a solution of tetralysin (Lys-Lys-Lys-Lys; SEQ ID NO: 4, 50 mg, 0.094 mmol) in water (1.5 mL) was added to this solution, and the mixture was stirred. Triethylamine (0.1 g) was further added, and the mixture was stirred at room temperature for 5 hr. After completion of the reaction, the insoluble material was filtered off, and the solvent was removed under reduced pressure in an evaporator. Then, ethyl acetate (10 mL) was added, and the mixture was dissolved. Sodium sulfate was added, and the mixture was stirred, filtrated and dehydrated. Hexane (20 mL) was added to the filtrate, the mixture was cooled to 0° C. or below, and the obtained crude crystals were collected by filtration. The crude crystals were dissolved in ethyl acetate (20 mL), Kyoward #2000 (0.01 g) and Kyoward#700 (0.1 g) were added as adsorbents, and the mixture was stirred at 40° C. for 0.5 hr. After the adsorbent was filtered off, hexane (100 mL) was added, and crystallization was performed by cooling. Further crystallization gave the object compound (1.2 g, yield 55%).

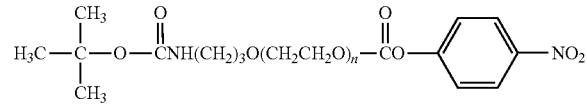

(8)

(2) Synthesis of aminbpropyl-polyoxyethylenecarbamyl-{Lys(aminopropyl-polyoxyethylene carbamyl)}$_4$<NH$_2$-PEG3400-{Lys(—PEG3400-NH$_2$)}$_4$>

The crystals obtained in (1) were dissolved in 2 N hydrochloric acid solution (20 mL), and the solution was stirred at 30° C. for 1 hr. After the reaction, the reaction solution was neutralized with 30% sodium hydroxide solution. Sodium chloride (10 g) was added and dissolved therein, and the mixture was extracted 3 times with chloroform. The obtained chloroform layer was dried over sodium sulfate and filtrated. Chloroform was evaporated, and the residue was concentrated. Toluene (5 mL) and ethyl acetate (5 mL) were added to the concentrated solution, and the mixture was dissolved by heating. Hexane (20 mL) was added to allow crystallization, and the obtained crystals were collected by filtration and dried to give (aminopropyl-polyoxyethylenecarbamyl)-{Lys (aminopropyl-polyoxyethylenecarbamyl)}$_4$, wherein the terminal amino was deprotected (0.8 g).

(3) Synthesis of maleimidepropylamidepropyl-polyoxyethylenecarbamyl-{Lys(maleimidepropylamidepropyl-polyoxyethylenecarbamyl)}$_4$<MAL-PEG3400-{Lys(-PEG3400-MAL)}$_4$ The crystals obtained in (2) were dissolved in acetonitrile (10 mL), and N-succinimidyl(3-maleimidepropionate) (SMP, 0.35 g) was added. Triethylamine (0.09 g) was further added, and the mixture was stirred at 40° C. for 5 hr. After the reaction, Kyoward 700 (0.05 g) and Kyoward 1000 (0.05 g) were added as adsorbents, and the mixture was further stirred at 40° C. for 0.5 hr. The reaction solution was filtrated, hexane (50 mL) was added to allow crystallization, and the crystals were collected by filtration. Ethyl acetate (10 mL) was added, the mixture was heated to dissolve the obtained crystals, and recrystallization was performed by addition of hexane (20 mL). The crystals were collected by filtration and dried to give maleimidepropylamidepropyl-polyoxyethylenecarbamyl-{Lysin(maleimidepropylamidepropyl-polyoxyethylenecarbamyl)}$_4$ (0.8 g).

(4) Synthesis of maleimidepropylamidepropyl-polyoxyethylenecarbamyl-{Lys(maleimidepropylamidepropyl-polyoxyethylenecarbamyl)}$_4$-succinimide ester <MAL-PEG3400-{Lys (-PEG3400-MAL)}$_4$-NHS>

The crystals obtained in (3) were dissolved in chloroform (10 mL) and, in the same manner as in Example 2 (3), maleimidepropylamidepropyl-polyoxyethylenecarbamyl-{Lys (maleimidepropylamidepropyl-polyoxyethylene carbamyl)}$_4$-succinimide ester was obtained as crystals (0.7 g).

The progress of the reaction and identification of the resultant product were performed in the same manner as in Example 1, and conversion of the spot of a methylpolyoxyethylene compound detected at Rf value of around 0.7-0.8 and the spot of peptide detected at Rf value of around 0.1 to the spot detected at Rf value of around 0.3-0.4 was confirmed by thin layer chromatography. For confirmation of the resultant product, methylpolyoxyethylene chain, peptide chain, succinimide ester and maleimide group (δ: around 6.8 ppm) were confirmed by $^1$H-NMR. The molecular weight of polyoxyethylene in the resultant product as determined by $^1$H-NMR was 17700.

For $^1$H-NMR analysis, JNM-ECP400 manufactured by JEOL Ltd. was used. $^1$H-NMR (CDCl$_3$, internal standard TMS)

The production scheme of Example 6 is shown below.

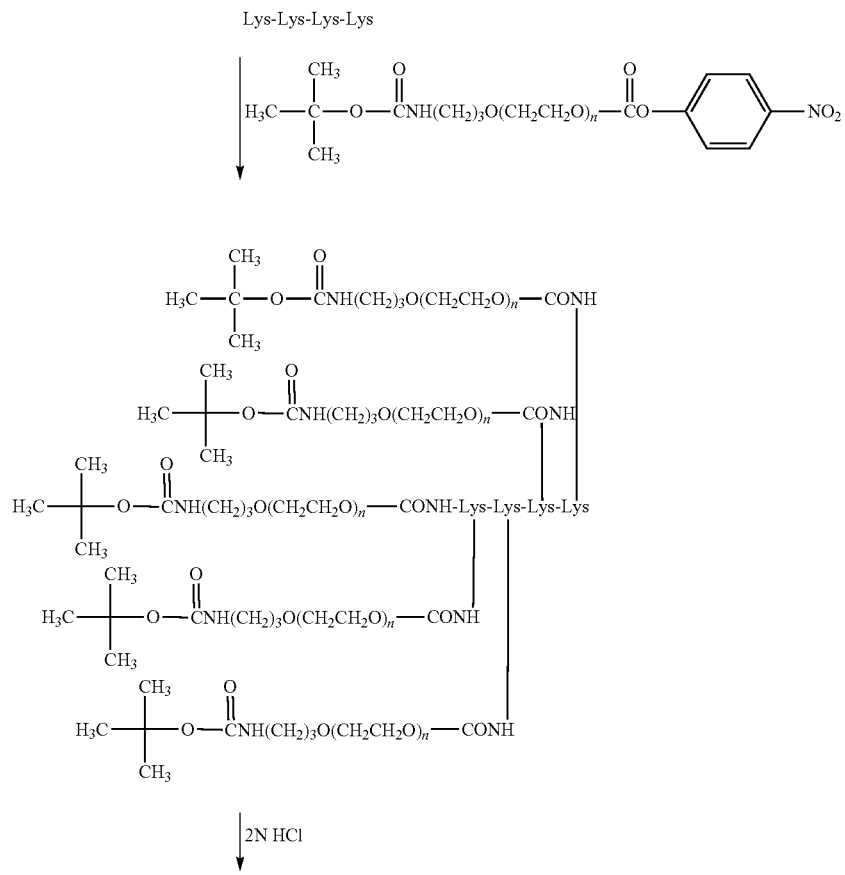

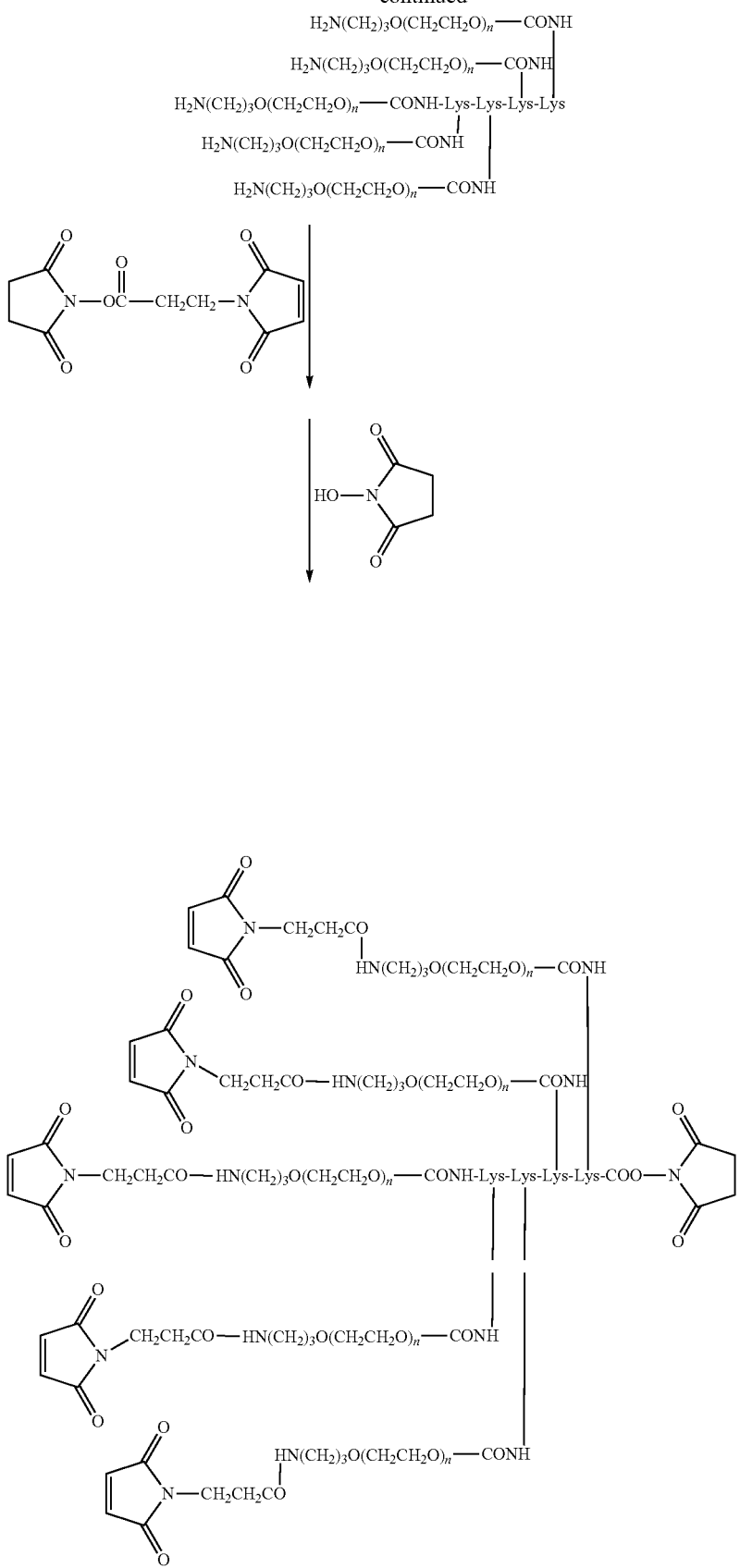

Example 7

Synthesis of p-nitrophenylcarbonyl-polyoxyethyleneoxypropylamino-{aspartic acid(-methyl-polyoxyethyleneoxypropylamide)}$_5$-glutaryloxy-methylpolyoxyethylene <pNP-PEG20000-{Asp(-PEG2000-OMe)}$_5$-PEG2000-OMe>

(1) Synthesis of benzylpolyoxyethyleneoxypropylamino-(benzylaspartic acid) 5<BE-PEG20000-BA$_5$>

Benzylpolyoxyethylene oxypropylamine (SUNBRIGHT BE-200PA, molecular weight 20000, 40 g) was dissolved in dichloromethane (500 mL) with heating to 40° C., β-benzyl L-aspartate N-carbonic anhydride (3 g, 6 equivalents) was added, and the mixture was reacted at 40° C. for 6 hr. After the reaction solution was allowed to cool to room temperature, a mixed solvent of ethyl acetate (1 L) and hexane (1 L) was added to allow crystallization. The crystals were washed with the same mixed solvent and dried to give the object compound BE-PEG20000-BA$_5$ as crystals (41.2 g).

(2) Synthesis of benzylpolyoxyethylene oxypropylamino-(benzylaspartic acid)$_5$-glutarate <BE-PEG20000-BA$_5$-GC>

To the crystals (19 g) obtained in (1) was added toluene (100 mL), sodium acetate (0.19 g) was added, and the mixture was dissolved at 55° C. Glutaric anhydride (1 g) was added, and the mixture was reacted at 55° C. for 9 hr. After the reaction, the insoluble material was filtered off, and hexan was added to the filtrate to allow crystallization. Using a mixed solvent of acetonitrile/ethyl acetate/hexane (1/8/8), crystallization was performed 3 times, and the crystals were washed with hexane and dried to give the object compound BE-PEG20000-BA$_5$-GC as crystals (16 g).

(3) Synthesis of hydropolyoxyethylene oxypropylamino-{aspartic acid (-methyl-polyoxyethylene oxypropylamide)}$_5$-glutarate <HO-PEG20000-{AA(-PEG2000-OMe)}$_5$-GC>

To the crystals (10 g) obtained in (2) was added 0.5 N aqueous sodium hydroxide solution (51 g), and the mixture was subjected to hydrolysis at room temperature for 24 hr. After the reaction, the reaction mixture was diluted with ion exchanged water (50 g), adjusted to pH 2 with phosphoric acid, and extracted twice with ethyl acetate (100 mL). Sodium chloride was added to the aqueous layer, and the mixture was extracted with chloroform (200 mL). After the extraction, the solvent was evaporated under reduced pressure, ethyl acetate (100 mL) was added, and the mixture was dissolved. Hexane (100 mL) was added to allow crystallization, and the crystals were washed with hexane and dried to give benzylpolyoxyethylene oxypropylamino-(aspartic acid)$_5$-glutarate <BE-PEG20000-AA$_5$-GC>(6 g).

To the obtained BE-PEG20000-AA$_5$-GC (2.5 g) was added toluene (25 mL), and the mixture was dissolved at 40° C. N-Hydroxysuccinimide (NHS, 0.25 g) was added, dicyclohexylcarbodiimide (DCC, 0.2 g) was added, and the mixture was reacted at 40° C. for 30 min. A solution of methylpolyoxyethylene oxypropylamine (SUNBRIGHT MEPA-20H, molecular weight 2000, 2.5 g) in toluene (12 mL) was added, and the mixture was reacted at 40° C. for 7 hr. After the reaction, the reaction solution was filtered, and hexane was added to allow crystallization. Using a mixed solvent of acetonitrile/ethyl acetate/hexane (10/80/80), crystallization was performed twice. The crystals were washed with hexane and dried to give benzylpolyoxyethylene oxypropylamino-{aspartic acid (-methyl-polyoxyethyleneoxypropyl amide)}$_5$-glutaryloxy-methylpolyoxyethylene <BE-PEG20000-{AA(-PEG2000-OMe)}$_5$-PEG2000-OMe>(1.8 g).

To the obtained BE-PEG20000-{AA(-PEG2000-OMe)}$_5$-PEG2000-OMe (1.95 g) was added 5% Pd/C (1.0 g), methanol (20 mL) and cyclohexene (3.3 mL) were added, and the mixture was heated to 55° C. and reacted for 2 hr. After the reaction mixture was allowed to cool to room temperature, chloroform was added, Pd/C was filtered off, and the solvent was removed under reduced pressure. The residue was dissolved in toluene (100 mL), and hexane was added to allow crystallization. The crystals were washed with hexane and dried to give the object compound HO-PEG20000-{AA(-PEG2000-OMe)}$_5$-GC as crystals (1.25 g).

(4) Synthesis of p-nitrophenylcarbonyl-polyoxyethyleneoxypropylamino-{aspartic acid (-methyl-polyoxyethyleneoxypropylamide)}$_5$-glutaryloxy-methylpolyoxyethylene <pNP-PEG20000-{Asp(-PEG2000-OMe)}$_5$-PEG2000-OMe>

The crystals (1 g) in obtained (3) were dissolved in toluene (10 mL), p-nitrophenylchloroformate (0.02 g) and triethylamine (0.015 g) were added, and the mixture was reacted at 80° C. for 9 hr. The reaction solution was filtered, and hexane was added to allow crystallization. Using a mixed solvent of ethyl acetate/hexane, crystallization was performed twice, and the crystals were washed with hexane and dried to give the object compound pNP-PEG20000-{Asp(-PEG2000-OMe)}$_5$-PEG2000-OMe as crystals (0.8 g).

For confirmation of the resultant product, methylpolyoxyethylene chain, peptide chain and p-nitrophenyl carbonate group (δ: around 8.2 ppm) were confirmed by 1H-NMR. The molecular weight of the resultant product as measured by the following GPC was 32100.

For GPC analysis, measurement was performed using LC-10A (Shimadzu) as a system. For analysis, GPC software (Shimadzu) was used. For GPC measurement values, analysis value at the main peak wherein the high molecular weight impurity and low molecular weight impurity were removed by perpendicularly cutting off from the inflection point to the baseline of the elution curve, and the analysis value of the whole peak from the elution starting point to the elution ending point were indicated alongside.

developing solvent: DMF flow rate: 0.7 mL/min column: PL gel MIXED-D X2 column temperature: 65° C.

sample amount: 40 mg/30 g, 0.1 mL detector: RI

Standard: PEG620, PEG4120, PEG11840, PEG32500, PEG74900

The production scheme of Example 7 is shown below.

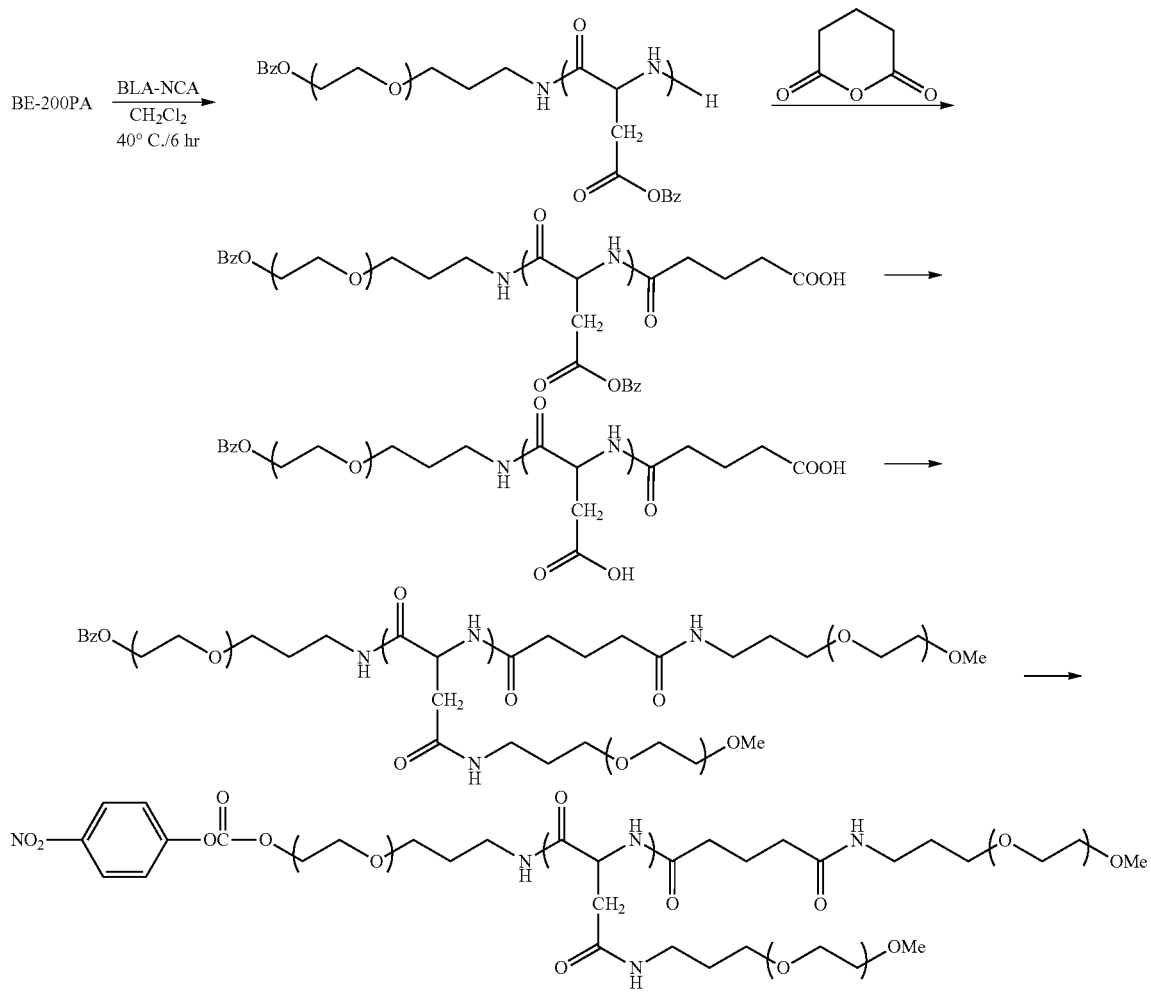

Example 8

Synthesis of methylpolyoxyethylene oxopentylcarbonyl-{Lys (methylpolyoxyethylene oxopentylcarbonyl)}$_4$-succinimide ester <ME-PEG20000-{Lys(-PEG20000-OMe)}$_3$-NHS>

(1) Synthesis of methylpolyoxyethyleneoxopentylcarbonyl-{Lys (methylpolyoxyethyleneoxopentylcarbonyl)}$_4$<ME-PEG20000-{Lys(-PEG20000-OMe)}$_3$>

α-Succinimidylcarboxypentyl-ω-methoxy-polyoxyethylene (SUNBRIGHT ME-200HS, weight-average molecular weight 20000, 4.37 g, 22 mmol) was dissolved in dimethylsulfoxide (10 mL), trilysin (Lys-Lys-Lys, 20 mg, 5 mmol) was added to this solution, and the mixture was stirred. Triethylamine (24 mg) was further added, and the mixture was stirred at 40° C. for 5 hr. After completion of the reaction, the insoluble material was filtered off. Ethyl acetate (50 mL) was added, the mixture was dissolved, and hexane (50 mL) was added to allow crystallization. Similar crystallization (twice) gave the object compound (2.9 g, yield 70%).

(2) Synthesis of methylpolyoxyethylene oxopentylcarbonyl-{Lys (methylpolyoxyethylene oxopentylcarbonyl)}$_3$-succinimide ester <ME-PEG20000-{Lys (-PEG20000-OMe)}$_3$-NHS>

To the crystals obtained in (1) (2 g) was add toluene (10 mL), and the mixture was dissolved at 40° C. N-hydroxysuccinimide (NHS, 4.3 mg) was added, dicyclohexylcarbodiimide (DCC, 13 mg) was added, and the mixture was reacted at 40° C. for 4 hr. After the reaction, the reaction solution was filtrated, and hexane was added to allow crystallization. Using a mixed solvent of acetonitrile/ethyl acetate/hexane (Oct. 80, 1980), crystallization was performed twice, and the crystals were washed with hexane and dried to give the object compound (2.9 g, yield 70%).

The progress of the reaction and identification of the resultant product were performed in the same manner as in Example 6, and conversion of the spot of a methylpolyoxyethylene compound detected at Rf value of around 0.7-0.8 and the spot of peptide detected at Rf value of around 0.1 to the spot detected at Rf value of around 0.3-0.4 was confirmed by thin layer chromatography. For confirmation of the resultant product, methylpolyoxyethylene chain, peptide chain and succinimide ester were confirmed by $^1$H-NMR. The molecular weight of polyoxyethylene in the resultant product as determined by GPC was 67800.

The production scheme of Example 8 is shown below.

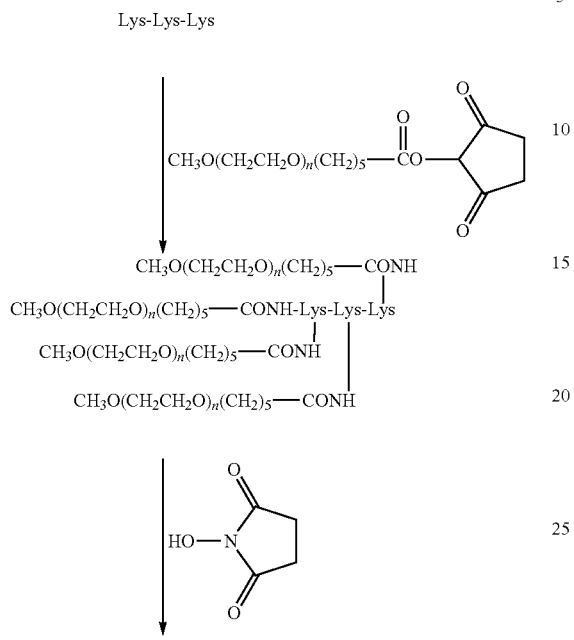

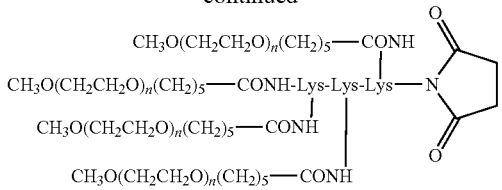

INDUSTRIAL APPLICABILITY

When the polyoxyalkylene derivative of the present invention is applied as a drug delivery system, and bound with a physiologically active substance such as protein and the like, one bond is capable of not only introducing polyoxyalkylene chains in a different number and having different properties such as molecular weight etc., but also controlling the stability by changing the binding mode thereof. Having plural functional groups, a physiologically active substance and an antibody etc. can be bound with each other, and a physiologically active substance and the like can be accumulated in the target site. As a result, selective delivery of the physiologically active substance to the target site can be improved, which in turn contributes to the reduction of side effects due to excessive administration.

This application is based on a patent application No. 2005-041523 filed in Japan, the contents of which are incorporated in full herein by this reference.

---

The invention claimed is:

1. A polyoxyalkylene derivative represented by the following formula (1)

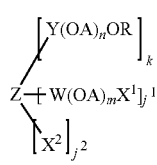

wherein

Z is a peptide residue consisting of 2 to 10 amino acid residues, wherein one or more amino acid residues have a side chain containing a functional group, OA is an oxyalkylene group having 2 to 4 carbon atoms, R is a hydrogen atom or a hydrocarbon group having 1 to 4 carbon atoms, $X^1$ is a group containing a succinimide group, a maleimide group, an amino group, a carboxyl group, a carbonate group, an aldehyde group, a sulfonyl group, a thiol group, or a vinyl group, $X^2$ is a group containing a succinimide group, a maleimide group, an amino group, a carboxyl group, a carbonate group, an aldehyde group, a sulfonyl group, a thiol group, a vinyl group, or a hydroxyl group, Y and W are each independently a divalent group containing a group selected from the group consisting of

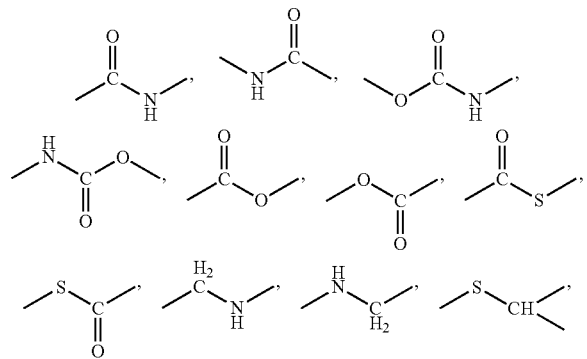

—S—S— and —O—, wherein at least one Y and/or W moiety differs from the remaining Y and W moieties, n is an integer of 5-1000, m is an integer of 5-800, $j^1$ is an integer of 0-8, $j^2$ is an integer of 0- 8, k is an integer of 0-8, wherein $1 \leq j^1+j^2 \leq 12$, $3 \leq k+j^1+j^2 \leq 12$, $30 \leq (n \times k)+(m \times j^1) \leq 2000$.

2. The polyoxyalkylene derivative of claim 1, wherein Z is a peptide residue consisting of 2 to 10 amino acid residues, wherein one or more amino acid residues have a side chain containing a functional group selected from the group consisting of an amino group, a carboxyl group, a thiol group and a hydroxyl group.

3. The polyoxyalkylene derivative of claim 2, wherein Z is a peptide residue consisting of 2 to 10 amino acid residues, wherein one or more amino acid residues are selected from the group consisting of lysine, aspartic acid, glutamic acid, cysteine and serine.

4. The polyoxyalkylene derivative of claim 3, wherein Z is a peptide residue consisting of 2 to 10 amino acid residues selected from the group consisting of lysine, aspartic acid and glutamic acid.

5. The polyoxyalkylene derivative of claim 1, wherein $j^1$ is 0, $j^2$ is 1-8 and k is 3-8.

6. The polyoxyalkylene derivative of claim 5, wherein $j^2$ is 1.

7. The polyoxyalkylene derivative of claim 1, wherein $j^1$ is 1-8.

8. The polyoxyalkylene derivative of claim 7, wherein $j^2$ is 0.

9. The polyoxyalkylene derivative of claim 7, wherein $j^1$ is 1.

10. The polyoxyalkylene derivative of claim 7, wherein $j^1$ 2-8.

11. The polyoxyalkylene derivative of claim 7, wherein $j^2$ is 1-8.

12. The polyoxyalkylene derivative of claim 1, wherein Z is a peptide residue consisting of 3 to 8 amino acid residues, wherein one or more amino acid residues are selected from the group consisting of glycine, lysine, glutamic acid, cysteine and aspartic acid.

13. The polyoxyalkylene derivative of claim 1, wherein R is a methyl group and OA is an oxyethylene group.

14. The polyoxyalkylene derivative of claim 1, wherein $X^1$ and $X^2$ are each independently a group selected from the group consisting of the following formulas (a)-(o):

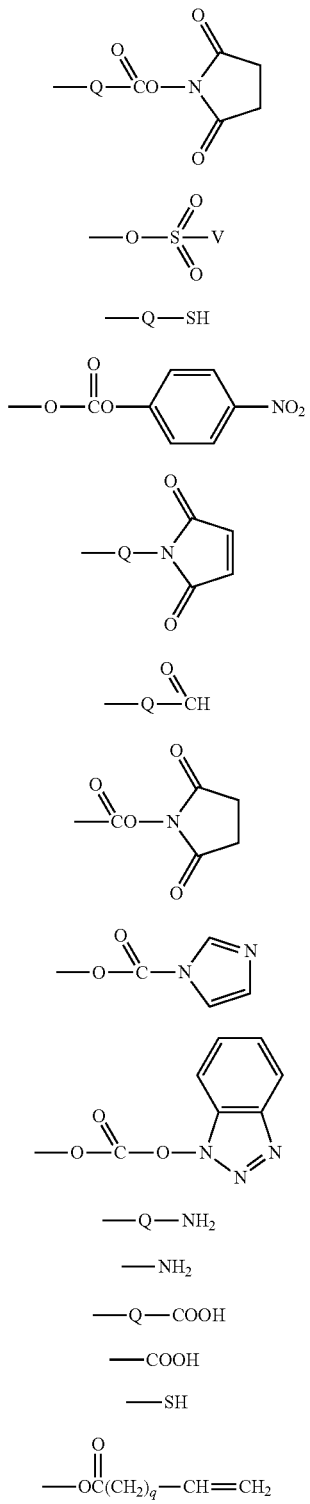

wherein Q is an alkylene group or an alkylene group having an ester bond, an amide bond, an ether bond, a urethane bond, a urea bond, a carbonate bond, a sulfide bond, an imine bond or a secondary amino group, V is a hydrocarbon group having 1 to 10 carbon atoms optionally containing a fluorine atom, and q is an integer of 1-6.

15. The polyoxyalkylene derivative of claim 8, wherein $j^1$ is 1.

16. The polyoxyalkylene derivative of claim 5, wherein $X^2$ is a group selected from the group consisting of the following formulas (a)-(o):

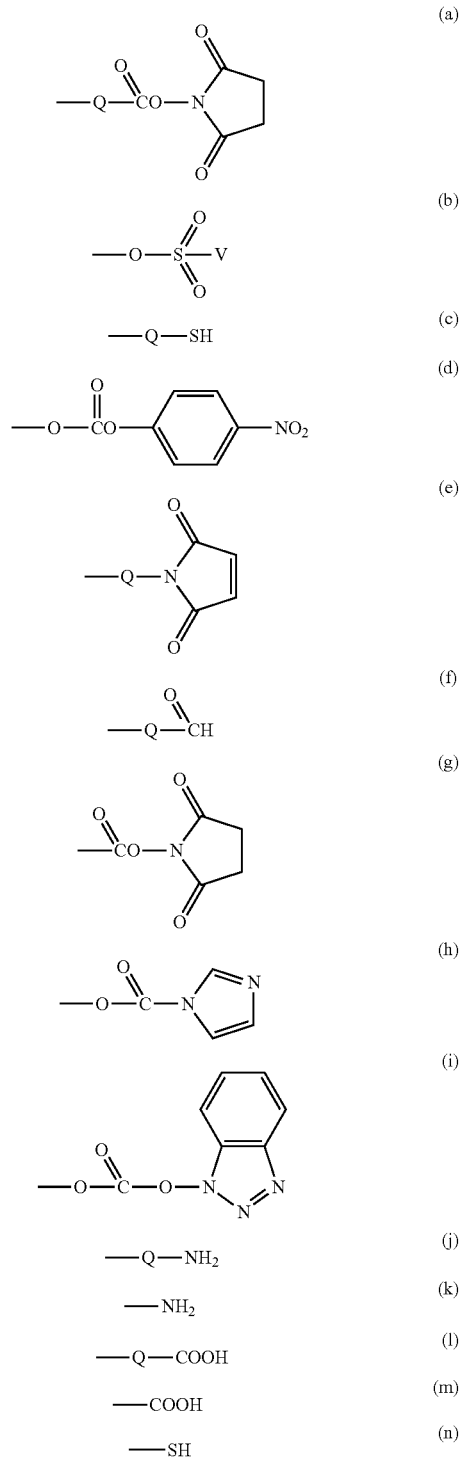

(o)

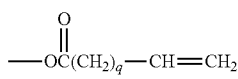

wherein Q is an alkylene group or an alkylene group having an ester bond, an amide bond, an ether bond, a urethane bond, a urea bond, a carbonate bond, a sulfide bond, an imine bond or a secondary amino group, V is a hydrocarbon group having 1 to 10 carbon atoms optionally containing a fluorine atom, and q is an integer of 1-6.

17. The polyoxyalkylene derivative of claim 7, wherein $X^1$ and $X^2$ are each independently a group selected from the group consisting of the following formulas (a)-(o):

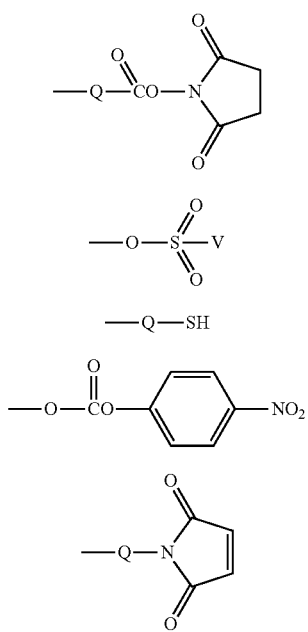

(a)

(b)

(c)

(d)

(e)

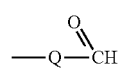 (f)

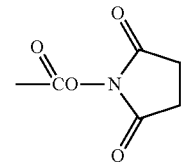 (g)

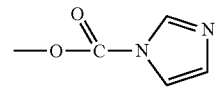 (h)

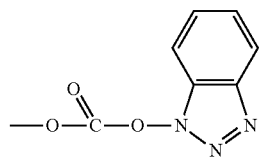 (i)

—Q—NH$_2$ (j)

—NH$_2$ (k)

—Q—COOH (l)

—COOH (m)

—SH (n)

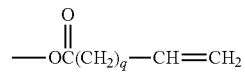 (o)

wherein Q is an alkylene group or an alkylene group having an ester bond, an amide bond, an ether bond, a urethane bond, a urea bond, a carbonate bond, a sulfide bond, an imine bond or a secondary amino group, V is a hydrocarbon group having 1 to 10 carbon atoms optionally containing a fluorine atom, and q is an integer of 1-6.

* * * * *

UNITED STATES PATENT AND TRADEMARK OFFICE
CERTIFICATE OF CORRECTION

PATENT NO.          : 8,012,488 B2
APPLICATION NO.     : 11/816611
DATED               : September 6, 2011
INVENTOR(S)         : Sakanoue et al.

It is certified that error appears in the above-identified patent and that said Letters Patent is hereby corrected as shown below:

In the claims:

Claim 1, at column 54, lines 28-29:

"0-8, wherein $1 \leq j^1+j^2 \leq 12$, $3 \leq k+j^1+j^2 \leq 12$, $30 \leq (n \times k)+(m \times j^1) \leq 2000$" should read "0-8, wherein $1 \leq j^1+j^2 \leq 12$, $3 \leq k+j^1 \leq 8$, $3 \leq k+j^1+j^2 \leq 12$, $30 \leq (n \times k)+(m \times j^1) \leq 2000$"

Signed and Sealed this
Third Day of April, 2012

David J. Kappos
*Director of the United States Patent and Trademark Office*